US010148126B2

(12) United States Patent
Hoarau et al.

(10) Patent No.: US 10,148,126 B2
(45) Date of Patent: Dec. 4, 2018

(54) WIRELESS ENERGY TRANSFER SYSTEM AND WEARABLES

(71) Applicant: TC1 LLC, St. Paul, MN (US)

(72) Inventors: Carine Hoarau, Pleasant Hill, CA (US); Jeffrey R. Lind, Danville, CA (US); Ian Coll McEachern, Sacramento, CA (US); John Nguyen, San Ramon, CA (US); Joanna M. Ignacio, Dunlin, CA (US); Chalan Koneru, Fremont, CA (US); John Curtis Layton, Livermore, CA (US); Nicole L. Parks, Crystal, MN (US); Leif A. Erickson, Minneapolis, MN (US); Serge Dubeau, Plymouth, MN (US); Martin A. Leugers, San Francisco, CA (US); Alex R. Brown, San Jose, CA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 15/252,981

(22) Filed: Aug. 31, 2016

(65) Prior Publication Data
US 2017/0063143 A1    Mar. 2, 2017

Related U.S. Application Data

(60) Provisional application No. 62/212,351, filed on Aug. 31, 2015.

(51) Int. Cl.
*H02J 7/02* (2016.01)
*A41D 27/20* (2006.01)
(Continued)

(52) U.S. Cl.
CPC ............... *H02J 50/10* (2016.02); *A41D 1/04* (2013.01); *A41D 13/1245* (2013.01);
(Continued)

(58) Field of Classification Search
CPC ...... H02J 7/025; H02J 50/10; A41D 13/1245; A41D 27/205; A41D 1/04; A41F 9/002;
(Continued)

(56) References Cited

U.S. PATENT DOCUMENTS

| 4,041,955 A | 8/1977 | Kelly et al. |
| 4,352,960 A | 10/1982 | Dormer et al. |

(Continued)

FOREIGN PATENT DOCUMENTS

| DE | 202012000166 U1 | 6/2013 |
| DE | 102012201073 A1 | 7/2013 |

(Continued)

OTHER PUBLICATIONS

Bonde et al.; Promise of unrestricted mobility with innovative, portable wireless powering of a mechanical circulatory assist device; American Association for Thoracic Surgery; © 2012; 2 pgs.; retrieved Mar. 12, 2014 from the internet: http://aats.org/annualmeeting/Abstracts/2012/T8.cgi.

(Continued)

*Primary Examiner* — Sun Lin
(74) *Attorney, Agent, or Firm* — Armstrong Teasdale LLP

(57) ABSTRACT

Disclosed are systems for wireless energy transfer including transcutaneous energy transfer. Embodiments are disclosed for user interface (UI) hubs to connect multiple batteries and to output system information to a patient. Embodiments are further disclosed for garments and devices to be worn by a patient requiring treatment. The garments are configured for a desired placement of a transmitter coil relative to a body of the patient and for facilitating patient comfort and quality of life. Methods for manufacturing and using the devices and the systems are also disclosed.

15 Claims, 30 Drawing Sheets

(51) Int. Cl.
*H02J 50/10* (2016.01)
*A41F 9/00* (2006.01)
*A41F 9/02* (2006.01)
*A61M 1/12* (2006.01)
*A41D 13/12* (2006.01)
*A41D 1/04* (2006.01)

(52) U.S. Cl.
CPC ....... *A41D 13/1281* (2013.01); *A41D 27/205* (2013.01); *A41F 9/002* (2013.01); *A41F 9/025* (2013.01); *A61M 1/127* (2013.01); *A61M 2205/8206* (2013.01); *A61M 2205/8237* (2013.01); *A61M 2205/8243* (2013.01); *A61M 2209/088* (2013.01)

(58) Field of Classification Search
CPC .......... A61M 1/127; A61M 2205/8237; A61M 2205/8206; A61M 2209/088
USPC .......................................................... 320/108
See application file for complete search history.

(56) References Cited

U.S. PATENT DOCUMENTS

| | | |
|---|---|---|
| 4,561,443 A | 12/1985 | Hogrefe et al. |
| 4,561,444 A | 12/1985 | Livingston et al. |
| 4,630,615 A | 12/1986 | Yomtov |
| 4,679,560 A | 7/1987 | Galbraith |
| 4,726,378 A | 2/1988 | Kaplan |
| 4,736,747 A | 4/1988 | Drake |
| 4,924,171 A | 5/1990 | Baba et al. |
| 4,945,305 A | 7/1990 | Blood |
| 5,070,223 A | 12/1991 | Colasante |
| 5,111,810 A * | 5/1992 | Fortney ............ A61F 7/02 602/2 |
| 5,346,458 A | 9/1994 | Affeld |
| 5,350,413 A | 9/1994 | Miller et al. |
| 5,569,156 A | 10/1996 | Mussivand |
| 5,630,836 A | 5/1997 | Prem et al. |
| 5,690,693 A | 11/1997 | Wang et al. |
| 5,702,431 A | 12/1997 | Wang et al. |
| 5,755,748 A | 5/1998 | Borza |
| 5,771,438 A | 6/1998 | Palermo et al. |
| 5,831,248 A | 11/1998 | Hojyo et al. |
| 5,948,006 A | 9/1999 | Mann |
| 6,123,726 A | 9/2000 | Mori et al. |
| 6,149,683 A | 11/2000 | Lancisi et al. |
| 6,212,430 B1 | 4/2001 | Kung |
| 6,296,533 B1 | 10/2001 | Grubbs et al. |
| 6,312,338 B1 | 11/2001 | Sato et al. |
| 6,320,354 B1 | 11/2001 | Sengupta et al. |
| 6,324,431 B1 | 11/2001 | Zarinetchi et al. |
| 6,327,504 B1 | 12/2001 | Dolgin et al. |
| 6,389,318 B1 | 5/2002 | Zarinetchi et al. |
| 6,400,991 B1 | 6/2002 | Kung |
| 6,442,434 B1 | 8/2002 | Zarinetchi et al. |
| 6,451,055 B1 | 9/2002 | Weiss |
| 6,458,164 B1 | 10/2002 | Weiss |
| 6,478,820 B1 | 11/2002 | Weiss |
| 6,553,263 B1 | 4/2003 | Meadows et al. |
| 6,579,315 B1 | 6/2003 | Weiss |
| 6,591,139 B2 | 7/2003 | Loftin et al. |
| 6,605,032 B2 | 8/2003 | Benkowski et al. |
| 6,647,298 B2 | 11/2003 | Abrahamson et al. |
| 6,650,213 B1 | 11/2003 | Sakurai et al. |
| 6,723,039 B2 | 4/2004 | French et al. |
| 6,772,011 B2 | 8/2004 | Dolgin |
| 6,801,807 B2 | 10/2004 | Abrahamson |
| 6,810,289 B1 | 10/2004 | Shaquer |
| 6,850,803 B1 | 2/2005 | Jimenez et al. |
| 6,894,456 B2 | 5/2005 | Tsukamoto et al. |
| 6,895,281 B1 | 7/2005 | Amundson et al. |
| 6,949,065 B2 | 9/2005 | Sporer et al. |
| 6,960,968 B2 | 11/2005 | Odendaal et al. |
| 6,967,621 B1 | 11/2005 | Cadotte, Jr. et al. |
| 6,985,773 B2 | 1/2006 | Von Arx et al. |
| 7,015,769 B2 | 3/2006 | Schulman et al. |
| 7,107,103 B2 | 9/2006 | Schulman et al. |
| 7,126,310 B1 | 10/2006 | Barron |
| 7,225,032 B2 | 5/2007 | Schmeling et al. |
| 7,246,040 B2 | 7/2007 | Borg et al. |
| 7,286,880 B2 | 10/2007 | Olson et al. |
| 7,428,438 B2 | 9/2008 | Parramon et al. |
| 7,471,986 B2 | 12/2008 | Hatlestad |
| 7,496,733 B2 | 2/2009 | Altman et al. |
| 7,505,816 B2 | 3/2009 | Schmeling et al. |
| 7,515,012 B2 | 4/2009 | Schulman et al. |
| 7,522,878 B2 | 4/2009 | Baarman |
| 7,532,901 B1 | 5/2009 | Lafranchise et al. |
| 7,565,187 B1 | 7/2009 | Dynok et al. |
| 7,571,007 B2 | 8/2009 | Erickson et al. |
| 7,574,173 B2 | 8/2009 | Terranova et al. |
| 7,587,241 B2 | 9/2009 | Parramon et al. |
| 7,599,743 B2 | 10/2009 | Hassler et al. |
| 7,650,187 B2 | 1/2010 | Gruber et al. |
| 7,650,192 B2 | 1/2010 | Wahlstrand |
| 7,711,433 B2 | 5/2010 | Davis et al. |
| 7,720,546 B2 | 5/2010 | Ginggen et al. |
| 7,724,303 B2 * | 5/2010 | DeSorbo ................ G03B 17/56 348/372 |
| 7,741,734 B2 | 6/2010 | Joannopoulos et al. |
| 7,761,164 B2 | 7/2010 | Verhoef et al. |
| 7,774,069 B2 | 8/2010 | Olson et al. |
| 7,782,190 B1 | 8/2010 | Martin et al. |
| 7,805,200 B2 | 9/2010 | Kast et al. |
| 7,812,481 B2 | 10/2010 | Iisaka et al. |
| 7,818,036 B2 | 10/2010 | Lair et al. |
| 7,818,037 B2 | 10/2010 | Lair et al. |
| 7,825,543 B2 | 11/2010 | Karalis et al. |
| 7,830,114 B2 | 11/2010 | Reed |
| 7,864,244 B2 * | 1/2011 | Desorbo ................ H04N 5/225 248/187.1 |
| 7,865,245 B2 | 1/2011 | Torgerson et al. |
| 7,872,367 B2 | 1/2011 | Recksiek et al. |
| 7,904,170 B2 | 3/2011 | Harding |
| 7,932,696 B2 | 4/2011 | Peterson et al. |
| 7,962,222 B2 | 6/2011 | He et al. |
| 7,986,367 B2 * | 7/2011 | Desorbo ................ G03B 17/56 320/107 |
| RE42,682 E | 9/2011 | Barreras et al. |
| 8,076,801 B2 | 12/2011 | Karalis et al. |
| 8,081,925 B2 | 12/2011 | Parramon et al. |
| 8,096,954 B2 | 1/2012 | Stahmann et al. |
| 8,140,168 B2 | 3/2012 | Olson et al. |
| 8,150,529 B2 | 4/2012 | Snell et al. |
| 8,165,694 B2 | 4/2012 | Carbunaru et al. |
| 8,185,212 B2 | 5/2012 | Carbunaru et al. |
| 8,193,766 B2 | 6/2012 | Rondoni et al. |
| 8,203,434 B2 | 6/2012 | Yoshida |
| 8,244,367 B2 | 8/2012 | Wahlstrand et al. |
| 8,247,926 B2 | 8/2012 | Issa et al. |
| 8,258,653 B2 | 9/2012 | Kitamura et al. |
| 8,265,770 B2 | 9/2012 | Toy et al. |
| 8,278,784 B2 | 10/2012 | Cook et al. |
| 8,292,052 B2 | 10/2012 | Bohori et al. |
| 8,299,652 B2 | 10/2012 | Smith et al. |
| 8,301,079 B2 | 10/2012 | Baarman |
| 8,319,473 B2 | 11/2012 | Choi et al. |
| 8,362,742 B2 | 1/2013 | Kallmyer |
| 8,373,310 B2 | 2/2013 | Baarman et al. |
| 8,378,522 B2 | 2/2013 | Cook et al. |
| 8,378,523 B2 | 2/2013 | Cook et al. |
| 8,463,395 B2 | 6/2013 | Forsell |
| 8,489,200 B2 | 7/2013 | Zarinetchi et al. |
| 8,551,163 B2 | 10/2013 | Aber et al. |
| 8,562,508 B2 | 10/2013 | Dague et al. |
| 8,581,793 B2 | 11/2013 | Carr |
| 8,587,154 B2 | 11/2013 | Fells et al. |
| 8,620,447 B2 | 12/2013 | D'Ambrosio et al. |
| 8,628,460 B2 | 1/2014 | Yomtov et al. |
| 8,629,578 B2 | 1/2014 | Kurs et al. |
| 8,668,473 B2 | 3/2014 | Larose et al. |
| 8,694,117 B2 | 4/2014 | Aghassian et al. |

(56) References Cited

U.S. PATENT DOCUMENTS

| | | |
|---|---|---|
| 8,810,071 B2 | 8/2014 | Sauerlaender et al. |
| 8,884,468 B2 | 11/2014 | Lemmens et al. |
| 8,909,351 B2 | 12/2014 | Dinsmoor et al. |
| 8,971,958 B2 | 3/2015 | Frikart et al. |
| 9,002,468 B2 | 4/2015 | Shea et al. |
| 9,106,083 B2 | 8/2015 | Partovi |
| 9,192,704 B2 | 11/2015 | Yomtov et al. |
| 9,302,093 B2 | 4/2016 | Mashiach |
| 9,515,494 B2 | 12/2016 | Kurs et al. |
| 9,515,495 B2 | 12/2016 | Kurs et al. |
| 9,560,787 B2 | 1/2017 | Kallmyer et al. |
| 2002/0038138 A1 | 3/2002 | Zarinetchi et al. |
| 2002/0087204 A1 | 7/2002 | Kung et al. |
| 2002/0093456 A1 | 7/2002 | Sawamura et al. |
| 2003/0171792 A1 | 9/2003 | Zarinetchi et al. |
| 2004/0138725 A1 | 7/2004 | Forsell |
| 2004/0256146 A1 | 12/2004 | Frericks |
| 2005/0006083 A1 | 1/2005 | Chen et al. |
| 2005/0090883 A1 | 4/2005 | Westlund et al. |
| 2005/0288743 A1 | 12/2005 | Ahn et al. |
| 2006/0199997 A1 | 9/2006 | Hassler et al. |
| 2006/0271129 A1 | 11/2006 | Tai et al. |
| 2007/0096686 A1 | 5/2007 | Jimenez et al. |
| 2007/0123948 A1 | 5/2007 | Dal Molin |
| 2007/0142696 A1 | 6/2007 | Crosby et al. |
| 2007/0191706 A1 | 8/2007 | Calderon et al. |
| 2008/0009198 A1 | 1/2008 | Marino |
| 2008/0027293 A1 | 1/2008 | Vodermayer et al. |
| 2008/0054638 A1 | 3/2008 | Greene et al. |
| 2008/0100294 A1 | 5/2008 | Rohling et al. |
| 2008/0149736 A1 | 6/2008 | Kim et al. |
| 2008/0167531 A1 | 7/2008 | McDermott |
| 2008/0211320 A1 | 9/2008 | Cook et al. |
| 2009/0018616 A1 | 1/2009 | Quick et al. |
| 2009/0051224 A1 | 2/2009 | Cook et al. |
| 2009/0072628 A1 | 3/2009 | Cook et al. |
| 2009/0081943 A1 | 3/2009 | Dobyns et al. |
| 2009/0174264 A1 | 7/2009 | Onishi et al. |
| 2009/0212736 A1 | 8/2009 | Baarman et al. |
| 2009/0226328 A1 | 9/2009 | Morello |
| 2009/0270679 A1 | 10/2009 | Hoeg et al. |
| 2009/0284220 A1 | 11/2009 | Toncich et al. |
| 2010/0019985 A1 | 1/2010 | Bashyam et al. |
| 2010/0033021 A1 | 2/2010 | Bennett |
| 2010/0035453 A1 | 2/2010 | Tronnes et al. |
| 2010/0045114 A1 | 2/2010 | Sample et al. |
| 2010/0063347 A1 | 3/2010 | Yomtov et al. |
| 2010/0066305 A1 | 3/2010 | Takahashi et al. |
| 2010/0069992 A1 | 3/2010 | Aghassian et al. |
| 2010/0102639 A1 | 4/2010 | Joannopoulos et al. |
| 2010/0109958 A1 | 5/2010 | Haubrich et al. |
| 2010/0114143 A1 | 5/2010 | Albrecht et al. |
| 2010/0116860 A1* | 5/2010 | Tello .................. A45F 3/04 224/576 |
| 2010/0122995 A1 | 5/2010 | Thomas et al. |
| 2010/0171368 A1 | 7/2010 | Schatz et al. |
| 2010/0184371 A1 | 7/2010 | Cook et al. |
| 2010/0194334 A1 | 8/2010 | Kirby et al. |
| 2010/0210233 A1 | 8/2010 | Cook et al. |
| 2010/0211134 A1 | 8/2010 | Forsell |
| 2010/0222848 A1 | 9/2010 | Forsell |
| 2010/0222849 A1 | 9/2010 | Forsell |
| 2010/0225174 A1 | 9/2010 | Jiang |
| 2010/0244576 A1 | 9/2010 | Hillan et al. |
| 2010/0253340 A1 | 10/2010 | Corum et al. |
| 2010/0256708 A1 | 10/2010 | Thornton et al. |
| 2010/0277121 A1 | 11/2010 | Hall et al. |
| 2010/0308939 A1 | 12/2010 | Kurs |
| 2010/0314946 A1 | 12/2010 | Budde et al. |
| 2010/0331919 A1 | 12/2010 | Digiore et al. |
| 2011/0025132 A1 | 2/2011 | Sato |
| 2011/0043050 A1 | 2/2011 | Yabe et al. |
| 2011/0046699 A1 | 2/2011 | Mazanec |
| 2011/0057607 A1 | 3/2011 | Carobolante |
| 2011/0101790 A1 | 5/2011 | Budgett |
| 2011/0109263 A1 | 5/2011 | Sakoda et al. |
| 2011/0115431 A1 | 5/2011 | Dunworth et al. |
| 2011/0127848 A1 | 6/2011 | Ryu et al. |
| 2011/0148215 A1 | 6/2011 | Marzetta et al. |
| 2011/0178361 A1 | 7/2011 | Yomtov |
| 2011/0181235 A1 | 7/2011 | Walley et al. |
| 2011/0205083 A1 | 8/2011 | Janna et al. |
| 2011/0234155 A1 | 9/2011 | Chen et al. |
| 2011/0241436 A1 | 10/2011 | Furukawa |
| 2011/0245892 A1 | 10/2011 | Kast et al. |
| 2011/0266880 A1 | 11/2011 | Kim et al. |
| 2011/0276110 A1 | 11/2011 | Whitehurst et al. |
| 2011/0278948 A1 | 11/2011 | Forsell |
| 2011/0291489 A1 | 12/2011 | Tsai et al. |
| 2011/0291613 A1 | 12/2011 | Rosik et al. |
| 2011/0295345 A1 | 12/2011 | Wells et al. |
| 2011/0298294 A1 | 12/2011 | Takada et al. |
| 2011/0301667 A1 | 12/2011 | Olson et al. |
| 2011/0313238 A1 | 12/2011 | Reichenbach et al. |
| 2012/0001485 A1 | 1/2012 | Uchida |
| 2012/0032522 A1 | 2/2012 | Schatz et al. |
| 2012/0039102 A1 | 2/2012 | Shinoda |
| 2012/0057322 A1 | 3/2012 | Waffenschmidt |
| 2012/0065458 A1 | 3/2012 | Tol |
| 2012/0080957 A1 | 4/2012 | Cooper et al. |
| 2012/0091951 A1 | 4/2012 | Sohn |
| 2012/0104997 A1 | 5/2012 | Carobolante |
| 2012/0109256 A1 | 5/2012 | Meskins et al. |
| 2012/0119914 A1 | 5/2012 | Uchida |
| 2012/0146575 A1 | 6/2012 | Armstrong et al. |
| 2012/0149229 A1 | 6/2012 | Kearsley et al. |
| 2012/0150259 A1 | 6/2012 | Meskens |
| 2012/0153739 A1 | 6/2012 | Cooper et al. |
| 2012/0153954 A1 | 6/2012 | Ota et al. |
| 2012/0157753 A1 | 6/2012 | D'Ambrosio |
| 2012/0157754 A1 | 6/2012 | D'Ambrosio |
| 2012/0158407 A1 | 6/2012 | Forsell |
| 2012/0161539 A1 | 6/2012 | Kim et al. |
| 2012/0164943 A1 | 6/2012 | Bennett |
| 2012/0169132 A1 | 7/2012 | Choudhary et al. |
| 2012/0169133 A1 | 7/2012 | Lisi et al. |
| 2012/0169137 A1 | 7/2012 | Lisi et al. |
| 2012/0169139 A1 | 7/2012 | Kudo |
| 2012/0169278 A1 | 7/2012 | Choi et al. |
| 2012/0175967 A1 | 7/2012 | Dibben et al. |
| 2012/0235364 A1 | 9/2012 | Wang et al. |
| 2012/0239118 A1 | 9/2012 | Ozawa et al. |
| 2012/0245649 A1 | 9/2012 | Bohori et al. |
| 2012/0245664 A1 | 9/2012 | Smith et al. |
| 2012/0259398 A1 | 10/2012 | Chen et al. |
| 2012/0274148 A1 | 11/2012 | Sung et al. |
| 2012/0306433 A1 | 12/2012 | Kim et al. |
| 2013/0007949 A1 | 1/2013 | Kurs et al. |
| 2013/0060103 A1 | 3/2013 | Bergida et al. |
| 2013/0119773 A1 | 5/2013 | Davis |
| 2013/0127253 A1 | 5/2013 | Stark et al. |
| 2013/0149960 A1 | 6/2013 | Dec et al. |
| 2013/0159956 A1 | 6/2013 | Verghese et al. |
| 2013/0190551 A1 | 7/2013 | Callaway et al. |
| 2013/0197607 A1 | 8/2013 | Wilder et al. |
| 2013/0214731 A1 | 8/2013 | Dinsmoor |
| 2013/0241306 A1 | 9/2013 | Aber et al. |
| 2013/0241468 A1 | 9/2013 | Moshfeghi |
| 2013/0271088 A1 | 10/2013 | Hwang et al. |
| 2013/0289334 A1 | 10/2013 | Badstibner et al. |
| 2013/0310630 A1 | 11/2013 | Smith et al. |
| 2013/0320773 A1 | 12/2013 | Schatz et al. |
| 2013/0331638 A1 | 12/2013 | Cameron et al. |
| 2014/0005466 A1 | 1/2014 | Crosby et al. |
| 2014/0011447 A1 | 1/2014 | Konanur et al. |
| 2014/0028110 A1 | 1/2014 | Petersen et al. |
| 2014/0028111 A1 | 1/2014 | Hansen et al. |
| 2014/0031606 A1 | 1/2014 | Hansen et al. |
| 2014/0152252 A1 | 6/2014 | Wood |
| 2014/0163644 A1 | 6/2014 | Scott et al. |
| 2014/0265620 A1 | 9/2014 | Hoarau et al. |
| 2014/0265621 A1 | 9/2014 | Wong et al. |
| 2014/0275727 A1 | 9/2014 | Bonde et al. |
| 2015/0123654 A1 | 5/2015 | Gagnon et al. |

(56) References Cited

U.S. PATENT DOCUMENTS

| | | |
|---|---|---|
| 2015/0207330 A1 | 7/2015 | Petersen |
| 2015/0207331 A1 | 7/2015 | Petersen |
| 2015/0222127 A1 | 8/2015 | Hansen |
| 2015/0222128 A1 | 8/2015 | Hansen |
| 2015/0222139 A1 | 8/2015 | Petersen et al. |
| 2015/0229289 A1 | 8/2015 | Suzuki |
| 2015/0290373 A1 | 10/2015 | Rudser et al. |
| 2016/0135684 A1 | 5/2016 | Kappel et al. |
| 2016/0218432 A1 | 7/2016 | Pope et al. |
| 2016/0250484 A1 | 9/2016 | Nguyen et al. |
| 2016/0254703 A1 | 9/2016 | Hansen |
| 2016/0254704 A1 | 9/2016 | Hansen et al. |
| 2016/0277879 A1* | 9/2016 | Daoura et al. ........ H04W 4/008 |

FOREIGN PATENT DOCUMENTS

| | | |
|---|---|---|
| EP | 0589608 A2 | 9/1993 |
| EP | 1513241 A1 | 3/2005 |
| EP | 2267864 A2 | 6/2010 |
| GB | 2477034 A | 7/2011 |
| JP | H03109063 A | 5/1991 |
| JP | 11-506646 | 6/1999 |
| JP | 2013094456 A | 5/2013 |
| JP | 2013161640 A | 8/2013 |
| JP | 2014160611 A | 9/2014 |
| KR | 1020020089605 | 11/2002 |
| KR | 1020120007296 | 1/2012 |
| KR | 1020120077448 | 7/2012 |
| WO | 0001442 A2 | 1/2000 |
| WO | 74747 A1 | 12/2000 |
| WO | 137926 A1 | 5/2001 |
| WO | 2005106901 A2 | 11/2005 |
| WO | 2007053881 A1 | 5/2007 |
| WO | 2008066941 A2 | 6/2008 |
| WO | 2009018271 A1 | 2/2009 |
| WO | 2009021220 A1 | 2/2009 |
| WO | 2009023905 A1 | 2/2009 |
| WO | 2009042977 A1 | 4/2009 |
| WO | 2010030378 A1 | 3/2010 |
| WO | 2010089354 A2 | 8/2010 |
| WO | 2011081626 A1 | 7/2011 |
| WO | 2011113934 A1 | 9/2011 |
| WO | 2012002063 A1 | 1/2012 |
| WO | 2012056365 A2 | 5/2012 |
| WO | 2012087807 A2 | 6/2012 |
| WO | 2012087811 A2 | 6/2012 |
| WO | 2012087816 A2 | 6/2012 |
| WO | 2012087819 A2 | 6/2012 |
| WO | 2012099965 A2 | 7/2012 |
| WO | 2012141752 A2 | 10/2012 |
| WO | 2013110602 A1 | 8/2013 |
| WO | 2013138451 A1 | 9/2013 |
| WO | 2014039673 A1 | 3/2014 |

OTHER PUBLICATIONS

Chargepoint, Inc.; -chargepoin+®; product brochure; 4 pgs.; © 2014; retrieved Mar. 12, 2014 from the internet: http://www.chargepoint.com/network/.

Dixon, Jr.; Eddy current losses in transformer windings and circuit wiring; Unitrode Corp. Seminar Manual (SEM600); Watertown, MA; 12 pgs.; 1988 (year of pub. sufficiently earlier than effective US filing date and any foreign priority date).

Evatran; PluglessTM Level 2 EV Charging System (3.3kW); product brochure; 7 pgs.; retrieved Mar. 12, 2014 from the internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Notification of Transmittal of the International Search Report and the Written Opinion of the International Searching Authority for PCT Application No. PCT/US2015/051474, dated Dec. 30, 2015.

Development and Implementation of RFID Technology, Ed. Cristina Turcu, Feb. 2009, pp. 28-30, 93-97.

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Merli, Francesco, et al.,"The Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

* cited by examiner

Coil Pocket    Off-center (to the left) zipper

Internal view of coil within pocket

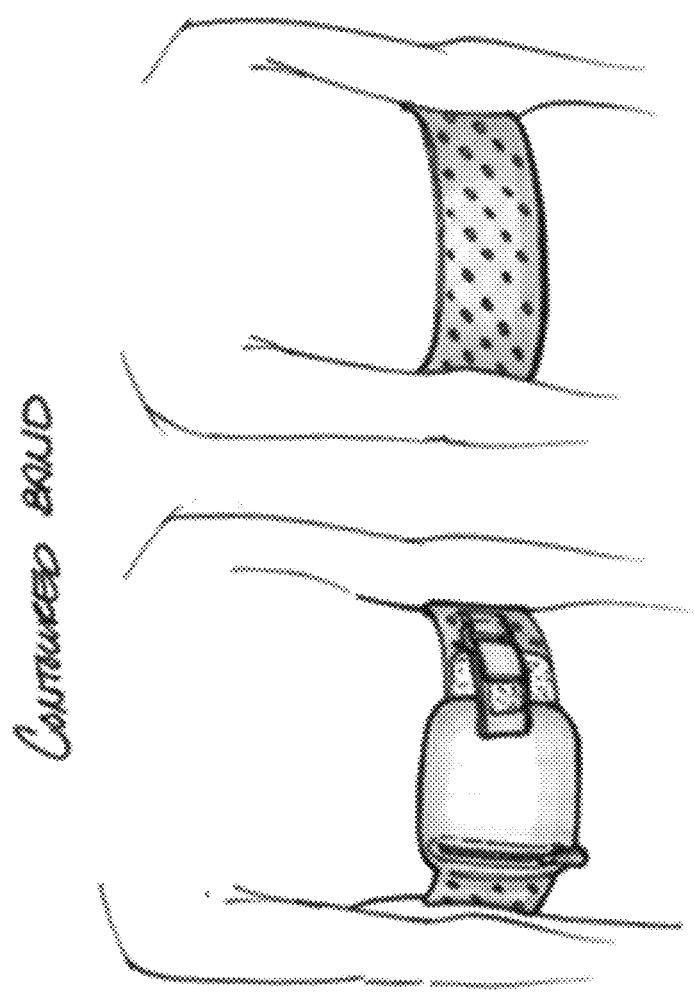

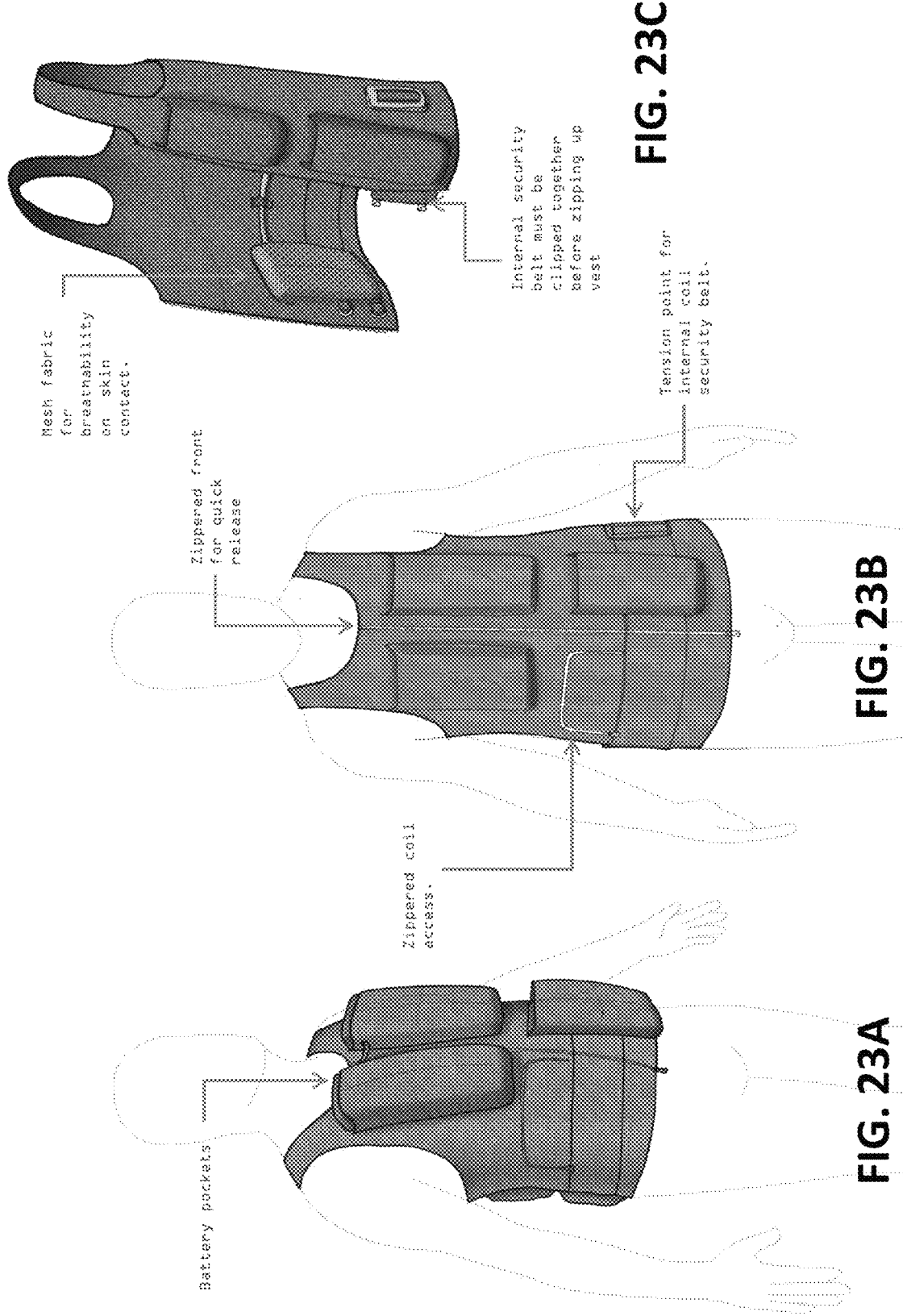

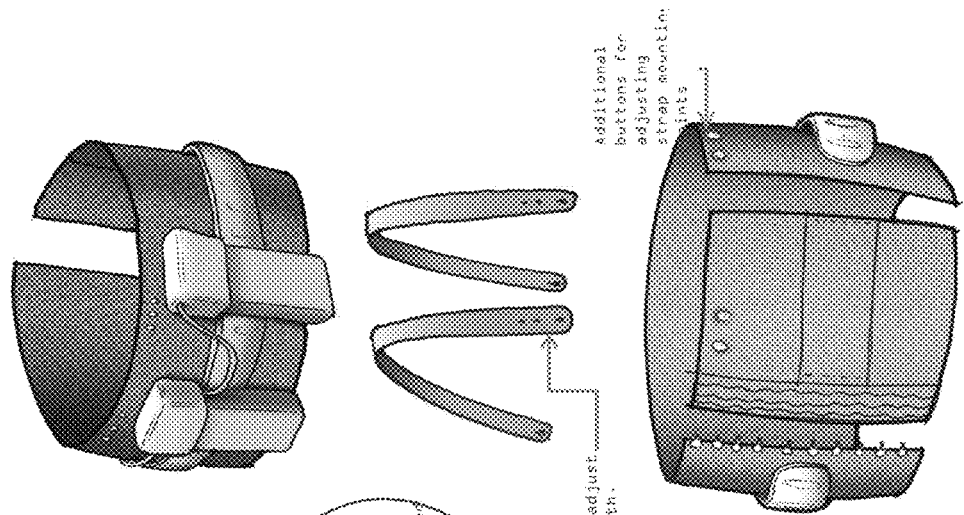
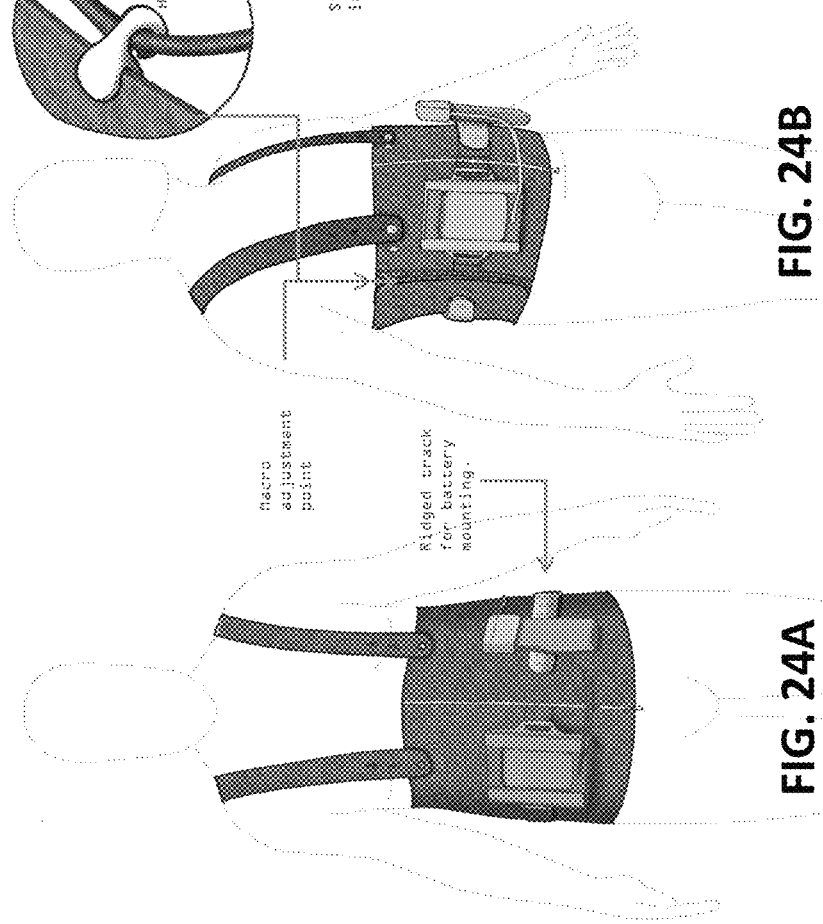
FIG. 24A  FIG. 24B  FIG. 24C  FIG. 24D

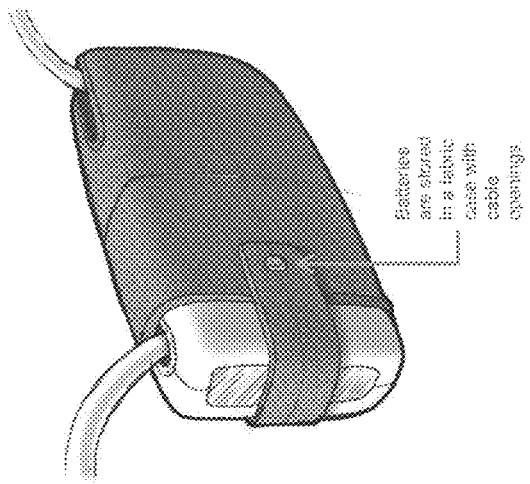
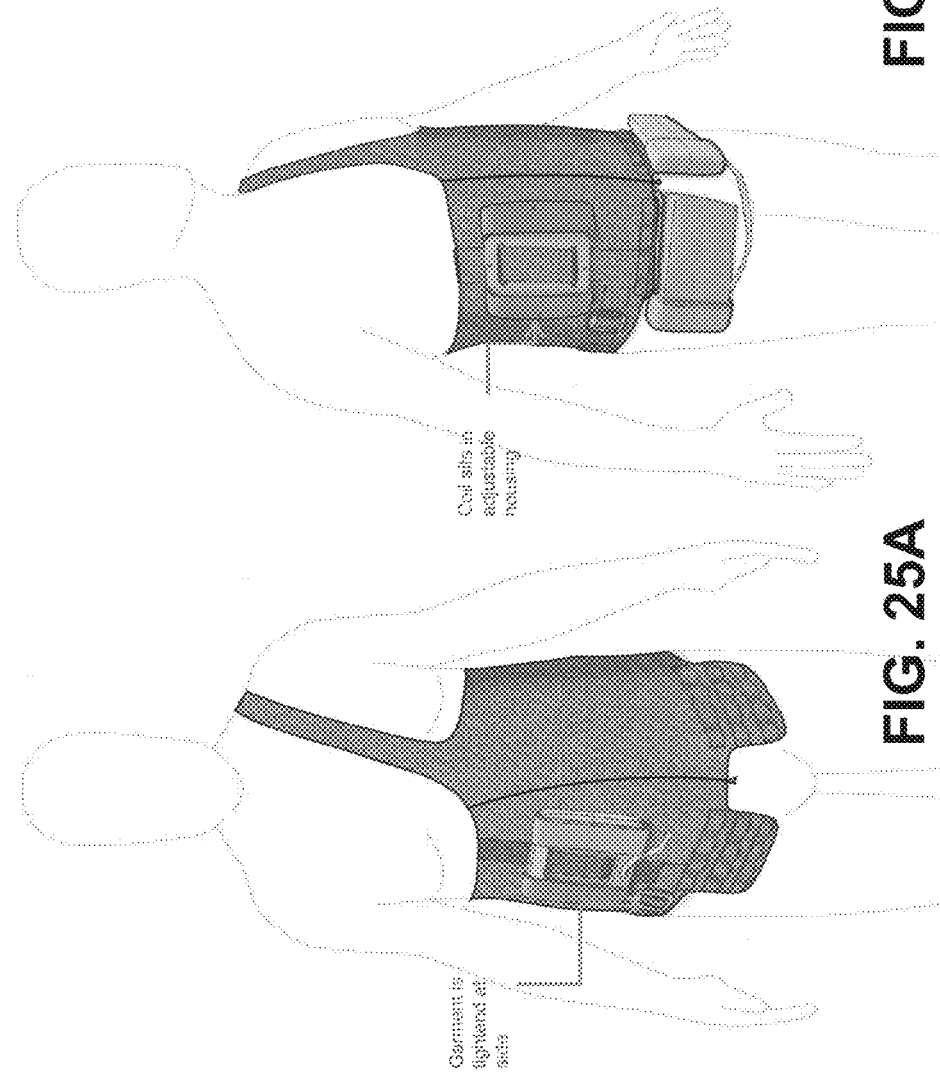
FIG. 25A  FIG. 25B  FIG. 25C

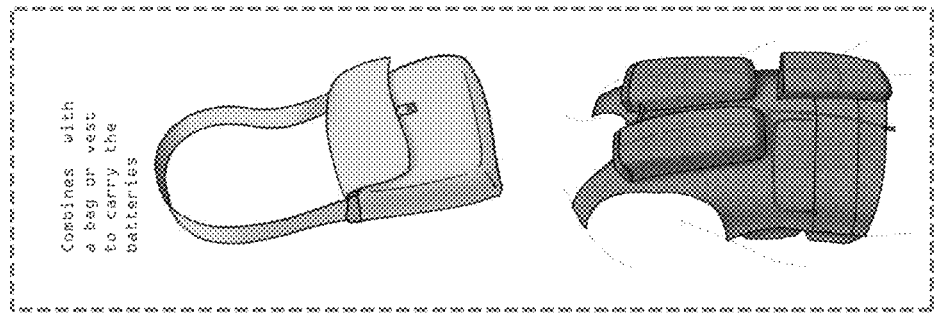
FIG. 27
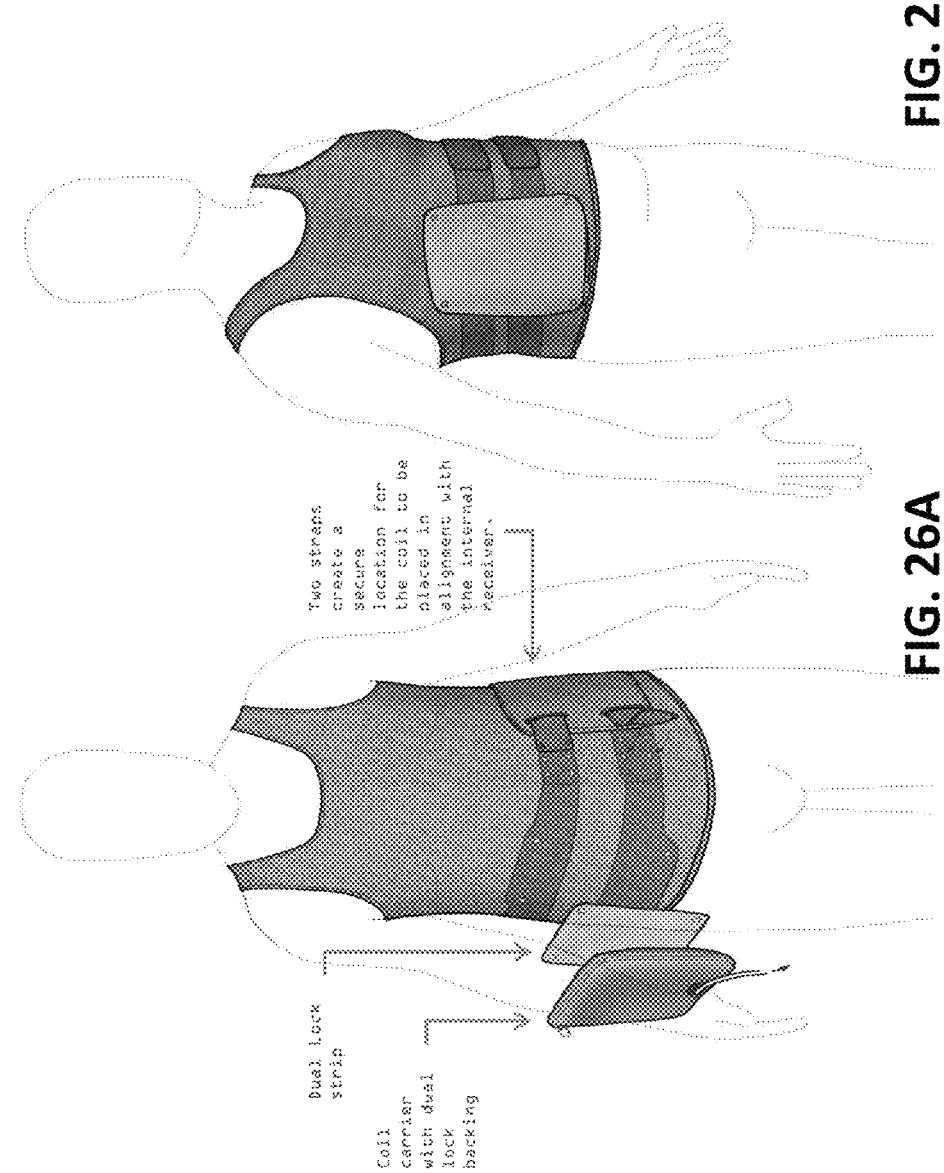
FIG. 26B
FIG. 26A

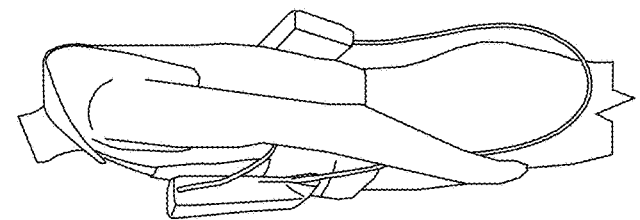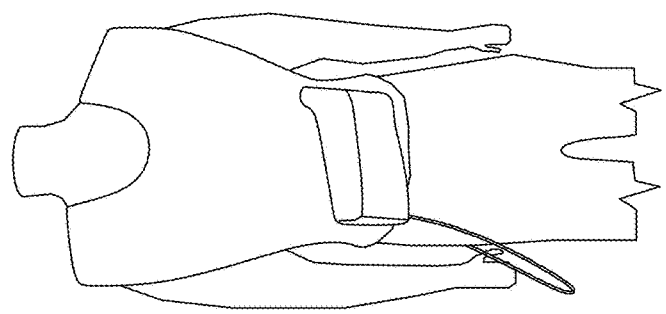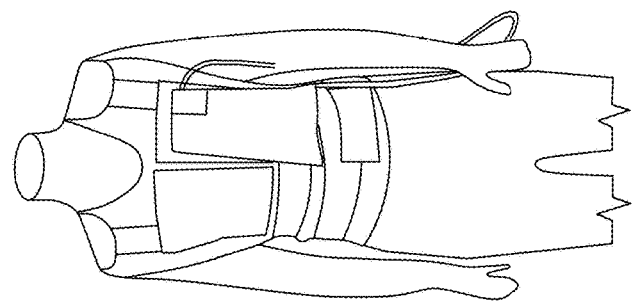
FIG. 28

WIRELESS ENERGY TRANSFER SYSTEM AND WEARABLES

CROSS-REFERENCE TO RELATED APPLICATIONS

This application claims the benefit of priority to U.S. Provisional Application No. 62/212,351, filed Aug. 31, 2015, the entire content and disclosure of which is hereby incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate to wireless energy transfer, and more specifically, to the transfer of energy from a power source outside the body to an implanted medical device inside the body.

BACKGROUND

Various techniques have been developed to transfer energy wirelessly, and in some cases over long distances. Examples of such systems include U.S. Pat. Nos. 6,327,504; 6,772,011; 7,825,543; and 8,076,801 and U.S. Pub. Nos. 2010/0102639 and 2010/010909445, the entire contents of which are incorporated herein for all purposes by reference.

More recently, there has been development into powering an implanted device wirelessly with a Transcutaneous Energy Transfer (TET) system. Many implantable medical devices require power sources or electrical systems to power the implant. Typically this is achieved using transcutaneous wiring to connect a power source to the implant. TET systems are designed to replace or supplement the transcutaneous wires.

TET systems typically include a lot of hardware and components. One example of a TET system includes the transmission of energy from a transmit coil to a receive coil using an oscillating magnetic field. The TET system also includes a power supply (e.g., battery and/or power conditioner to connect to AC mains) and processing electronics (e.g., solid state electronics and a controller), and other components. It can be burdensome for a patient to carry all these components, in particular for life-saving devices which must be carried at all times. Furthermore, TET systems often require precise alignment of components. Accordingly, there is a need for improvements to peripherals for carrying the necessary system components.

There is also the need for improved utilization and positioning of TET components. Modern medical devices typically require maximal power efficiency. For example, pumps such as ventricular assist devices (VAD) require a relatively high level of sustained and continuous power. With the advances of medical technology, there are an increasing number of implanted medical devices which can benefit from improvements in wireless energy transmission. Improvements in power usage can translate to meaningful reductions in the form factor of the internal power storage (e.g., battery). Improvements in power transmission can also lead to improvements in operation. For example, a slight improvement in power efficiency can mean significant increases in run time on the battery thus improving patient quality of life (QoL).

TET systems by their nature are sensitive to changes in the system. Even small relative changes to the relative orientation between the transmit and receive coil—distance or angle—can lead to a dramatic increase or decrease in power transmission. Indeed, many modern TET systems can only withstand a separation distance on the order of millimeters and require the coils to be generally in desired alignment. Any deviations can drop the power transmission efficiency below acceptable levels. Some existing TET systems for implantable medical devices require the implanted receiver coil to be positioned just under the skin, and typically include a mechanical feature to maintain exact alignment between the receive and transmit coils. However, by implanting these devices directly under the skin, the size and power requirements of these implanted devices is limited if they are to be powered by a TET system. Moreover, many TET systems are system to changes even within an operational range. For example, if one coil is moving or vibrating rapidly with respect to the other coil the power efficiency will drop dramatically.

The lack of effective positioning systems means that many TET systems are designed for placement of the transmit and receive coils directly adjacent each other in the pectoral region. The pectoral region is known to be relatively stable during activity due to the minimal amount of soft tissue and fat. There is less variability from patient to patient. In part for this reason the pectoral region is a common placement for implantable cardioverter defibrillators (ICD).

Accordingly, there is a need for devices and methods for addressing these and other problems. There is a need for systems and methods that reduce the burden on the patient and improve power transmission. There is the need for improvements to wearable devices for use with wireless energy transfer systems, and in certain respects TET systems.

SUMMARY OF THE DISCLOSURE

The present invention relates to a wireless energy transfer system, and more particularly, to wearable devices and garments for a wireless energy transfer system.

One aspect of the invention relates to a garment to be worn by a patient requiring treatment, the garment comprising a body portion configured for wrapping around at least a thoracic region of a patient's body, at least one strap configured to drape over a shoulder of the patient, at least one pocket sized and shaped to receive a battery for powering an implantable medical device, and at least one pocket for maintaining a transmitter coil at a desired location relative to the patient's body. In various embodiments, the coil pocket is formed of a non-metal. The at least one coil pocket may be positionable on a plurality of positions of the body portion. The at least one battery pocket may be positionable on a plurality of positions of the body portion.

One aspect of the invention relates to an accessory carrier for a patient requiring treatment, comprising a carrier having an interior for holding components of a medical system, the carrier including a first clip for securing a battery and a divider for separating the battery from the remainder of the interior, a flap covering at least a portion of the carrier, a strap for draping the carrier over a patient's body, and a closure for sealing the flap against the carrier.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 6A shows selected external components of an exemplary TET system including batteries and a coil for a VAD. FIG. 6B shows the basic components of a TETS system on a patient.

FIG. 10A is a front view of a patient. FIG. 10B is a back view of the patient.

FIG. 15A is a front view of a wearable device, illustrating the device opened into a flat position. FIG. 15B is a schematic view of the device of FIG. 15A, illustrating the inside of the band. FIGS. 15C, 15D, and 15E are back, front, and side views of the band on a patient.

FIGS. 17A to 17C are several views of another wearable device similar to the device of FIG. 15A, illustrating a modified band and connector to improve patient comfort and accommodate greater adjustments by the patient.

FIG. 18A is a front view of the device. FIG. 18B is a perspective view of the device, illustrated with batteries in the pockets.

FIG. 19A is a front perspective view of the device connected to a battery. FIG. 19B is a rear perspective view of the device, illustrated with a flap closure opened to allow removal of the battery.

FIG. 20A is an exploded front view of the device including a belt, clip, and battery pocket. FIG. 20B is an enlarged view of the battery clip.

FIG. 21A is a front view of the bag. FIG. 21B are perspective views of the bag, illustrating the bag in open and closed positions.

FIGS. 23A-23C illustrates a wearable device similar to the device of FIG. 11A. FIG. 23A is a front perspective view, illustrating the device worn on a body. FIG. 23B is a front view, illustrating the device worn on a body. FIG. 23C is a front perspective view, illustrating the device in an open position and detailing a pocket on the inner side of the device.

FIGS. 24A-24D illustrates a wearable device similar to the device of FIG. 11A. FIG. 24A is a front perspective view, illustrating the device worn on a body. FIG. 24B is a front view, illustrating the device worn on a body. FIG. 24C is an enlarged detail view of the clip of the device of FIG. 24B. FIG. 24D is an exploded view of the device of FIG. 24A.

FIGS. 25A-25C illustrates a wearable device similar to the device of FIG. 11A. FIGS. 25A and 25B are front perspective views, illustrating the device worn on a body. FIG. 25C is an enlarged detail view of the battery case of the device of FIG. 25A.

FIGS. 26A and 26B illustrates a wearable device similar to the device of FIG. 11A. FIG. 26A is a front perspective view, illustrating the device worn on a body with the coil carrier detached. FIG. 26B is a front view, illustrating the coil carrier attached to the main body portion.

FIG. 27 consists of several views of various wearable devices for use with the device of FIGS. 26A and 26B.

FIG. 28 consists of several views of another wearable device similar to the device of FIG. 11A.

DETAILED DESCRIPTION

Figure 1:
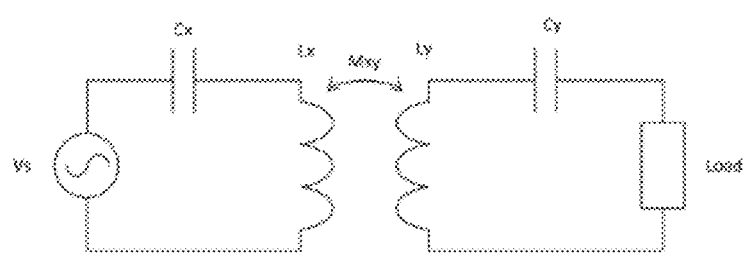
FIG. 1 illustrates a basic wireless energy transfer (WET) system.

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

FIGS. 1-4 illustrate a basic wireless energy transmission (WET) system. The exemplary system is a configured to transmit energy wireless using resonant coils and an oscillating magnetic field.

Various aspects of the system are similar to those described in International Patent Pub. No. WO2013110602; WO2012045050; U.S. Pat. Nos. 8,562,508; 8,140,168; 7,865,245; 7,774,069; 7,711,433; 7,650,187; 7,571,007; 7,741,734; 7,825,543; 6,772,011; 6,591,139; 6,553,263; 6,327,504; and 5,350,413; and U.S. Pub. Nos. 2014/0028110; 2013/0127253; 2013/0007949; 2010/0308939; 2008/027293; 2007/0123948; 2010/0114143; and 2010/0102639, the entire contents of which patents and applications are incorporated herein for all purposes.

Although important aspects of the inventions are directed to peripherals and wearable devices for a WET system, the design of the devices are typically informed by the performance constraints of the underlying WET system. Accordingly, the basic principles of the WET system will be described below.

Wireless Energy Transfer

With reference to FIG. 1, power may be transmitted wirelessly by magnetic induction. In various embodiments, the transmitter and receiver are closely coupled.

In some cases "closely coupled" or "close coupling" refers to a system that requires the coils to be very near each other in order to operate. For example, in some exemplary cases the external coil is directly adjacent the skin and the internal coil must be implanted subcutaneously just below the external coil.

In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter. In some cases, "loosely coupled" or "loose coupling" refers a highly resonant system and/or a system using strongly-coupled magnetic resonators.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. Exemplars of closely coupled system with resonant coils is described in International Pub. Nos. WO2001/037926; WO2012/087807; WO2012/087811; WO2012/087816; WO2012/087819; WO2010/030378; and WO2012/056365, U.S. Pub. No. 2003/0171792, and U.S. Pat. No. 5,350,413, incorporated herein for all purposes by reference.

In the following description and claims, the terms "coupled" along with its derivatives, may be used. It should be understood that the term "coupled" is used to indicate that two or more elements, which may or may not be in direct physical or electrical contact with each other, cooperate or interact with each other. The terms "energy transfer," "power transfer," and "power transmission," and their derivatives, are used interchangeably and refers to the transmission of energy between two devices.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antennas, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the invention will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In general, the system in accordance with various embodiments of this disclosure may include any system for wireless transmitting energy over a distance. The system generally includes one or more components for transmitting and receiving the energy. The energy may take various forms such as an electromagnetic field.

With reference to FIGS. 1-4, the exemplary system comprises one or more transmitters configured to transmit power wirelessly to one or more receivers. In various embodiments, the system includes a transmitter and more than one receiver in a multiplexed arrangement. A frequency generator may be electrically coupled to the transmitter to drive the transmitter to transmit power at a particular frequency or range of frequencies. The frequency generator can include a voltage controlled oscillator and one or more switchable arrays of capacitors, a voltage controlled oscillator and one or more varactors, a phase-locked-loop, a direct digital synthesizer, or combinations thereof. The transmitter can be configured to transmit power at multiple frequencies simultaneously. The frequency generator can include two or more phase-locked-loops electrically coupled to a common reference oscillator, two or more independent voltage controlled oscillators, or combinations thereof. The transmitter can be arranged to simultaneously delivery power to multiple receivers at a common frequency.

In various embodiments, the transmitter is configured to transmit a low power signal at a particular frequency. The transmitter may transmit the low power signal for a particular time and/or interval. In various embodiments, the transmitter is configured to transmit a high power signal wirelessly at a particular frequency. The transmitter may transmit the high power signal for a particular time and/or interval.

In various embodiments, the receiver includes a frequency selection mechanism electrically coupled to the receiver coil and arranged to allow the resonator to change a frequency or a range of frequencies that the receiver can receive. The frequency selection mechanism can include a switchable array of discrete capacitors, a variable capacitance, one or more inductors electrically coupled to the receiving antenna, additional turns of a coil of the receiving antenna, or combinations thereof.

In general, most of the flux from the transmitter coil does not reach the receiver coil. The amount of flux generated by the transmitter coil that reaches the receiver coil is described by "k" and referred to as the "coupling coefficient."

In various embodiments, the system is configured to maintain a value of k in the range of between about 0.2 to about 0.01. In various embodiments, the system is configured to maintain a value of k of at least 0.01, at least 0.02, at least 0.03, at least 0.04, or at least 0.05.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver in the exemplary system, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

FIG. 1 illustrates a simplified circuit for wireless energy transmission (WET). The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$Mxy = k\sqrt{Lx \cdot Ly}$$

In the exemplary system the power source Vs is in series with the transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. In an exemplary embodiment, the load an operative element such as an implanted medical device. In various embodiments, the load is one of a rechargeable power source and an operative element. For example, the receiver may be connected to a DC bus which is in turn connected to various components requiring power. These components may include, but are not limited to, a power source (e.g., battery), an operative medical device, a telemetry system, and associated circuitry. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (not shown) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, PL, is assumed to be 15 Watts and the operating frequency of the system, f, is 250 kHz. Then, for each cycle the load removes a certain amount of energy from the resonance:

$$e_L = \frac{P_L}{f} = 60 \; \mu J \quad \text{Energy the load removes in one cycle}$$

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 µJ.

The exemplary circuit was analyzed and the self-inductance of the receiver coil was found to be 60 uH. From the energy and the inductance, the voltage and current in the resonator could be calculated.

$$e_y = \frac{1}{2}Li^2$$

$$i_y = \sqrt{\frac{2e_y}{L}} = 3.74 \; A \; peak$$

$$v_y = \omega L_y i_y = 352 \; V \; peak$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given that k is 0.05:

$$e_x = \frac{420 \; \mu J}{0.05} = 8.4 \; mJ$$

For the same circuit the self inductance of the transmitter coil was 146 uH as mentioned above. This results in:

$$i_x = \sqrt{\frac{2e_x}{L}} = 10.7 \; A \; peak$$

$$v_x = \omega L_x i_x = 2460 \; V \; peak$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

One can also appreciate from the above that the form factor and weights of the various WET components may depend to a large degree on the WET performance criteria.

Figure 2:
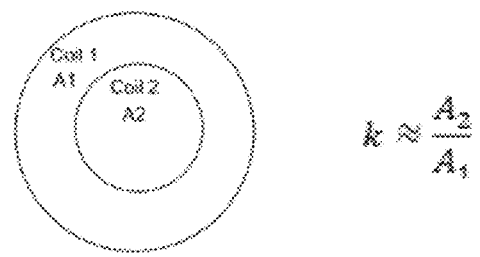
FIG. 2 illustrates the flux generated by a pair of coils.
Figure 3A:
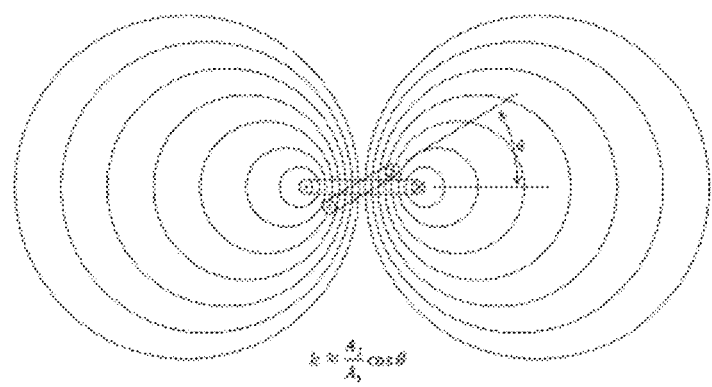
FIGS. 3A and 3B illustrate the effect of coil alignment on the coupling coefficient.
Figure 3B:
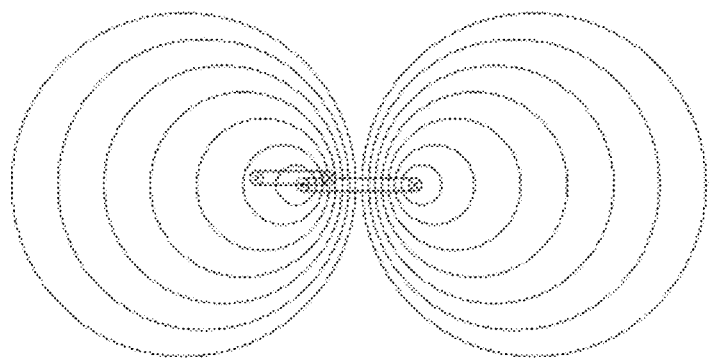

Turning to FIGS. 2, 3A, and 3B, the coupling coefficient and mutual inductance in view of the coil alignment will be explained.

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and ceteris paribus, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

U.S. Pub. No. 2014/0028110 to Petersen et al., incorporated herein for all purposes by reference, describes several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta (θ) is 90 degrees, the flux will not be received by the receiver and the coupling coefficient will be zero.

If the coils are arranged such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy}=M_{yx}$$

In an exemplary embodiment, the WET system is a TET system for an implanted medical device such as a blood pump. Systems and methods are provided herein for wirelessly transmitting power from an external power transmitter to a separate power receiver. The TET systems described herein can be configured to wirelessly transmit power from a transmitter positioned outside of a human body to a receiver implanted within the body. The receiver can be coupled to circuitry and a power source to power and operate an implantable medical device coupled to the receiver.

Figure 4:
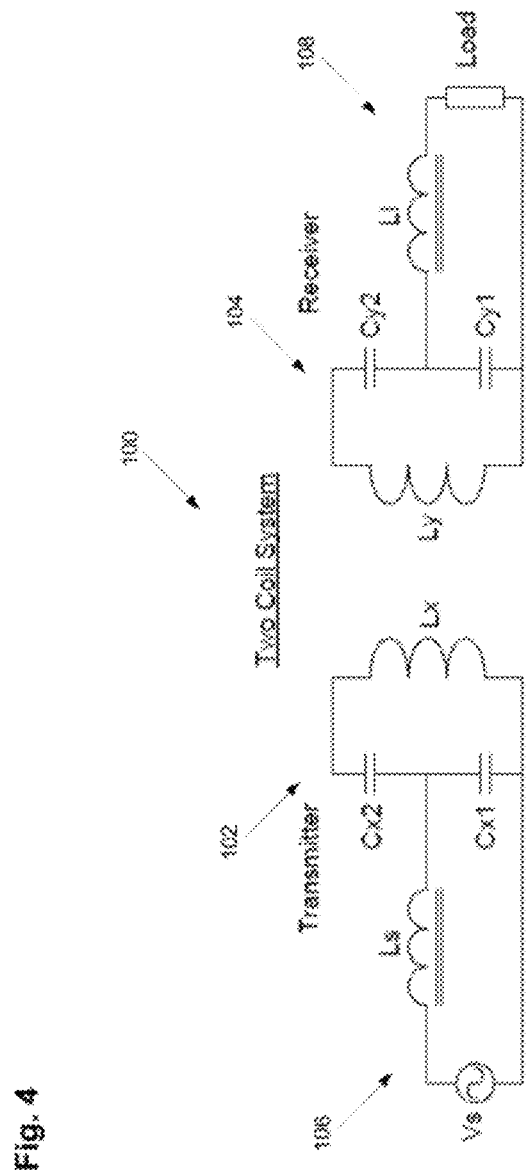
FIG. 4 illustrates half of an exemplary two-coil system for WET having a transmitter and a receiver.

FIG. 4 is an exemplary circuit diagram of half of an exemplary TET circuitry in accordance with the above. In practice the other half of the circuitry mirrors what is shown in FIG. 4. In some embodiments, the resonant systems described herein can operate at high voltages (possibly greater than 1000 Vac rms) to transmit the high power levels required by some implantable applications. For example, power levels of as high as approximately 10 W, 15 W, or more are typically required for a fully implanted LVAD system. In these embodiments, a voltage divider can be used in the TET system so that the load of the receiver resonator and power source of the transmitter resonator can operate at a lower voltage than other parts of the LVAD system. The voltage of the driving circuit and load can be dictated by a battery pack, which is typically in the range of 12-20 Vdc.

In one embodiment shown in FIG. 4, a TET system 100 comprises two resonant systems, a transmitter resonator 102 and a receiver resonator 104. Each of the resonant systems can be connected to a voltage divider circuit. Transmitter resonator 102 includes an inductor Lx and a capacitor Cx2 configured as a tank circuit. Receiver resonator 104 includes an inductor Ly and a capacitor Cy2 configured as a tank circuit. In order to excite each resonant system an impedance matching circuit can connect the transmitter resonator to the power source and the receiver resonator to the load. This way the load and power source only have to supply the real part of the power, and the reactive part of the power is handled by the impedance matching circuit.

In FIG. 4, the impedance matching circuits can comprise voltage dividers formed from capacitors. Voltage divider 106 can be coupled to transmitter resonator 102 and can comprise capacitor Cx1 and inductor Ls, coupled to voltage source Vs. Voltage divider 108 can be coupled to receiver resonator 104 and can comprise capacitor Cy1 and inductor L1, coupled to the Load. An additional inductor may be needed in series with the source and load. In a practical circuit the source is most likely a FET push pull circuit operating as a square wave voltage source. The output of the voltage source should not be placed directly across a capacitor or there will be extremely large currents on the switching transitions.

Many drive circuits are possible in addition to the FET push pull circuit (class-D amplifier). These include variations on resonant power amplifiers (classes B, C, and E) or self resonant circuits such as a Royer oscillator. Linear amplifiers (classes A and A-B) will also work, but will have lower efficiency.

In a further embodiment, at least one of the resonators 502 and 512 is coupled to a tunable resistor or an array or network of resistive elements to tune a quality factor "Q" of the system to maximize a voltage gain at the receiver unit 511. A tunable resistor is a circuit or component with a variable resistance value that can be changed in response to a control input. The control input may be voltage, current, or any other input that can cause the materials or circuit of the tunable resistor to change its resistance value. Similarly, an array or network of resistive elements can be configured to form different series and/or parallel arrangements of resistive elements to achieve an effective resistance value. For example, the resistive elements can be resistors, capacitors with effective resistance values, or a combination of both. In an embodiment, an array of resistive elements can be an array of capacitors, where the capacitors have the same capacitance values but different effective series resistance values. This allows the effective resistance to be adjusted while keeping the effective capacitance the same.

Figure 5:
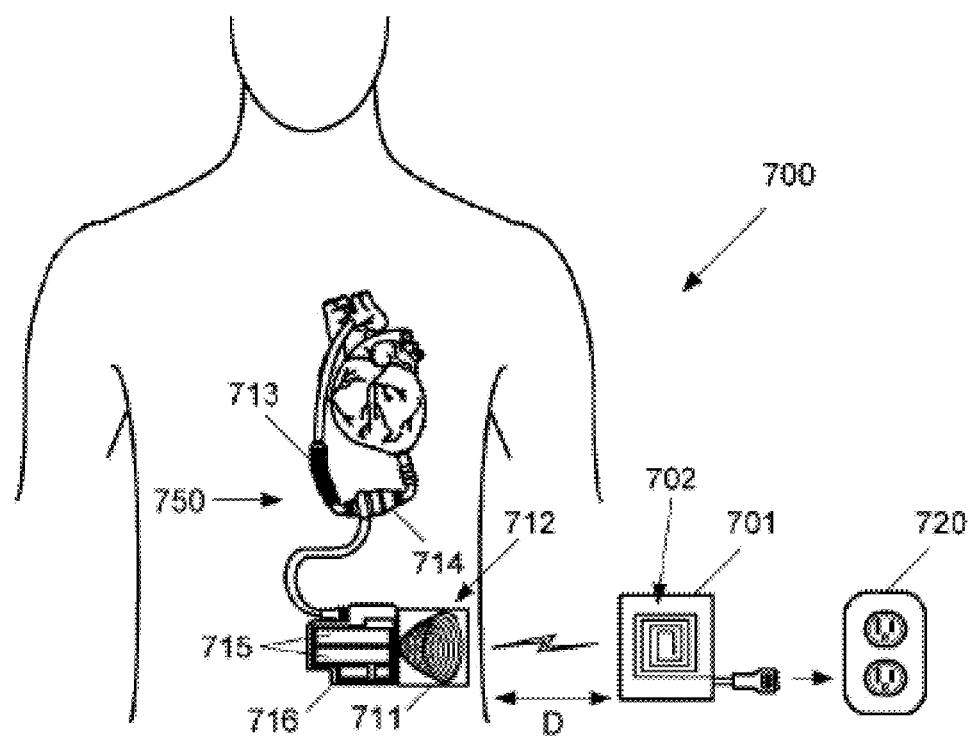
FIG. 5 is a basic implementation of a transcutaneous energy transfer (TET) system, illustrating operation with power from AC mains.

Turning to FIG. 5, an exemplary system 700 in accordance with the various inventions is shown. The exemplary system described has a relatively high quality factor. The quality factor "Q" describes the inverse power loss of the resonator. Hence, a larger Q means a lower power loss in the resonator and a higher energy transfer efficiency, resulting in a higher voltage gain at the receiver unit 711. The quality factor "Q" of a resonant system that has a transmitter resonator 702 and a receiver resonator 712 can be described by the square root of the product of the quality factors of the two resonators 702 and 712. In order to reduce the power loss in the system 700 to maximize the voltage gain at the receiver unit 711, the quality factor "Q" of the system can be increased by increasing the quality factors of either or both resonators 702 and 712. This can be achieved by tuning a tunable resistor or an array of resistive elements that is coupled to the coil of the respective resonator to modulate and to match the impedance seen by the resonator. Alternatively, a tunable or network of capacitive and/or inductive elements can be used to adjust the effective capacitance and/or the effective inductance to change the quality factor "Q."

Exemplary Ventricular Assist System Using Transcutaneous Energy Transfer

FIG. 5 illustrates exemplary embodiments of a transcutaneous energy transfer system (TETS) 700 with a ventricular assist device (VAD) 750 according to embodiments of the present invention. A VAD is a mechanical circulatory device that is used to partially or completely replace the function of a failing heart. For patients suffering from congestive heart failure, the VAD is implanted into the patient for support of the natural pumping function of a heart requiring assistance. VADs are designed to assist either the right (RVAD) or left (LVAD) ventricle, or both at once (BiVAD). VADs can be designed with an axial flow, centrifugal flow, or mixed flow configuration. An impeller is typically suspended by a journal bearing such as a ball and cup, or by a combination of active and/or passive magnetic forces, or by a combination of passive magnetic forces and hydrodynamic forces. In other embodiments, the blood pump can be an artificial heart, which is designed to completely take over cardiac function and may require the removal of a patient's heart.

The exemplary VAD 750 includes a pump assembly 713 including a blood pump 714, a rechargeable power storage device 716, and a power receiver unit 711, which are all implanted in the body. The rechargeable power storage device 716 may include two or more rechargeable batteries 715 to provide the VAD 750 with a backup battery in case the stored energy in the primary battery is depleted or if the primary battery fails otherwise. The rechargeable power storage device 716 can be implanted in a location away from the blood pump assembly 713, for example, in the lower abdominal as shown in FIG. 7A. The power receiving unit 711 includes a resonator 712 with a coil that is coupled to the power storage device 716, which is the electrical load of the power receiver unit 711. The receiver unit 711 is implanted in the lower abdominal area where there may be less spatial constraints on the size and shape of the receiver resonator 712 compared to the pocket in which the pump is positioned. The resonant frequency of the exemplary receiver resonator 712 can be in a range of 100 kHz to 10 MHz. In an exemplary embodiment, the resonant frequency of the receiver resonator 712 can be 100 kHz, 500 kHz, 1 MHz, or 10 MHz. In other embodiments, another resonant frequency that is safe for the human body can be used.

The TETS 700 also includes a power transmitter unit 701 that is external to the patient. The transmitter unit 701 includes a transmitter resonator 702 with a coil that is configured to be coupled to a power supply source 720 such as an electrical wall outlet. Additionally or alternatively, the transmitter unit 701 can be coupled to other power sources such as a battery that can be used to drive an electrical current through the coil of the transmitter resonator 702. When the transmitter unit 701 is plugged into the electrical wall outlet 720, an electrical current is generated in the coil of the transmitter resonator 702. The exemplary resonant frequency of the transmitter resonator 702 can be in a range of 100 kHz to 10 MHz. In an exemplary embodiment, the resonant frequency of the transmitter resonator 702 can be 100 kHz, 500 kHz, 1 MHz, or 10 MHz. In other embodiments, another resonant frequency that is safe for the human body can be used. The transmitter resonator 702 as part of the transmitter unit 701 may be embedded in a stationary object such as a wall, a chair, a bed, or other fixtures such as a car seat or objects that do not move by themselves without external control or human assistance. The source of power for a stationary and embedded transmitter resonator is generally alternating current (AC) from an electric outlet, but can also be direct current (DC) from a battery source. Likewise, the power signal may need to be converted between AC and DC depending on the pump type.

The exemplary system 700 includes one or more non-planar resonators. In the illustrated embodiment, the transmitter resonator 702 is a planar resonator made of a planar wire loop. The receiver resonator 712 is a non-planar resonator. In particular, the exemplary resonator has a curvature and is formed in a frustoconical shape. One will appreciate from the description herein that the size and shape of the resonators may vary depending on the application. Factors affecting the coil geometry include, but are not limited to, the designed for coupling zone between the receiver and transmitter, expected movement between the receiver and transmitter during use, and configuration of peripherals (e.g., controller and batteries).

When the receiver unit 711 in the patient comes within a separation distance D of the transmitter unit 701, the TETS 700 is able to wirelessly transfer energy from the transmitter unit 701 to the receiver unit 711 to recharge the power storage device 716 of the VAD 750. In one embodiment, at a given separation distance D being in the range of 2.5 cm to 35 cm, the transmitter unit 701 is able to deliver power in the range of 5 W to 20 W to the receiver unit 711 to recharge the batteries 715 in the power storage device 716 of the VAD 750. By using a non-planar coil in the receiver resonator 712 in the receiver unit 711, the TETS 700 is able to achieve a power transfer between the transmitter coil in the transmitter resonator 702 and the receiver coil in the receiver resonator 712 at a given separation distance D that is at least 25% of a maximum achievable power transfer at that given separation distance D, regardless of the coils' respective orientation to each other. For example, in one embodiment, the TETS 700 is able to transfer a maximum amount of 20 W at a distance D of 10 cm when the respective coils in the receiver and transmitter resonators 702 and 712 are in their ideal alignment. As the patient moves around and causes the coil in the receiver resonator 712 to be orientated at a different angle relative to the coil in the transmitter resonator 702 away from their ideal alignment, the TETS 700 is still able to transfer at least 5 W of power to the receiver unit 711 at the separation distance D of 10 cm. In other embodiments, a greater or lesser amount of power can be delivered over longer distances, for example, separation distances of 35 cm and beyond, by adjusting the size and geometries of the resonators.

The use of a non-planar resonator that spans a surface area occupying three spatial dimensions in the receiver unit 711 according to embodiments of the present invention has the advantage over conventional systems that uses only planar resonators, in that the non-planar receiver resonator 712 is able to couple with more magnetic flux generated from the transmitter unit 701 in a wider range of spatial orientations. Hence, at a given separation distance D within an operating range of the TETS 700, there is no requirement that the resonators 702 and 712 have to be placed in a particular orientation with respect to each other in order to transfer a meaningful amount of power required to recharge the rechargeable storage device 716.

As will be described below, in various embodiments the transmitter resonator 702 is part of a piece of wearable clothing such as a vest or a jacket, or other wearable accessories. In the case of a transmitter resonator that is embedded into a piece of clothing or object wearable by a person that moves with a person, the source of power may be a portable-sized rechargeable battery worn by the patient. The power source for the transmitter may also include AC mains and other power source configurations. Exemplars of various power source configurations for a VAD system employing TETS are disclosed in International Pub. No. WO2007/053881 to Glanzmann et al. and U.S. Pub. No. 2014/0005466 to Crosby et al., the entire contents of which are incorporated herein for all purposes by reference.

In various embodiments, the system is configured as a hybrid making use of TETS and a percutaneous driveline. Such a system is comparable to the TETS described above except a driveline for providing power and data through the skin is further provided. In various embodiments, the system makes use of a conventional driveline. In various embodiments, the system includes a driveline which can be detached for a period of time. An example of such a system is described in U.S. Pat. No. 8,562,508 to Dague et al., the entire contents of which are incorporated herein for all purposes for reference. Such a configuration provides additional flexibility and may also have reduced technical complexity.

One will appreciate from the description herein that these various configurations may affect the number and type of implantables and peripherals worn by the patient. Although the invention is described below in terms of TETS, one will appreciate that the principles can apply equally to other system configurations.

Figure 6A:
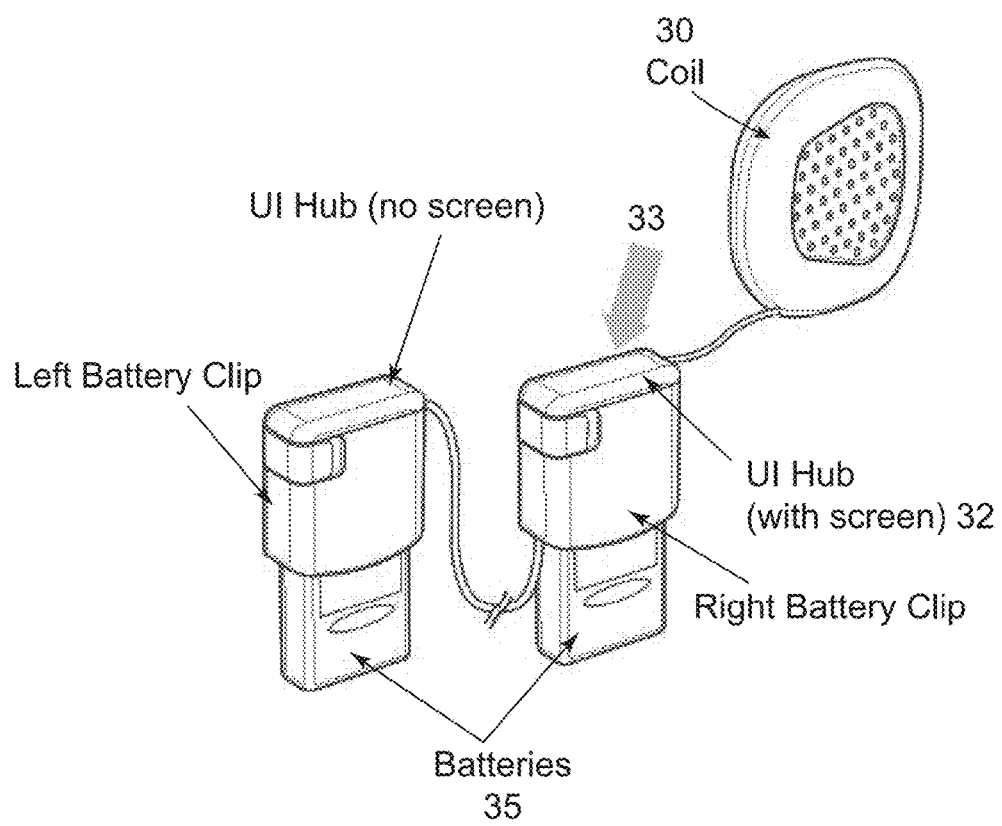
FIGS. 6A and 6B show components of an exemplary TET system.
Figure 6B:
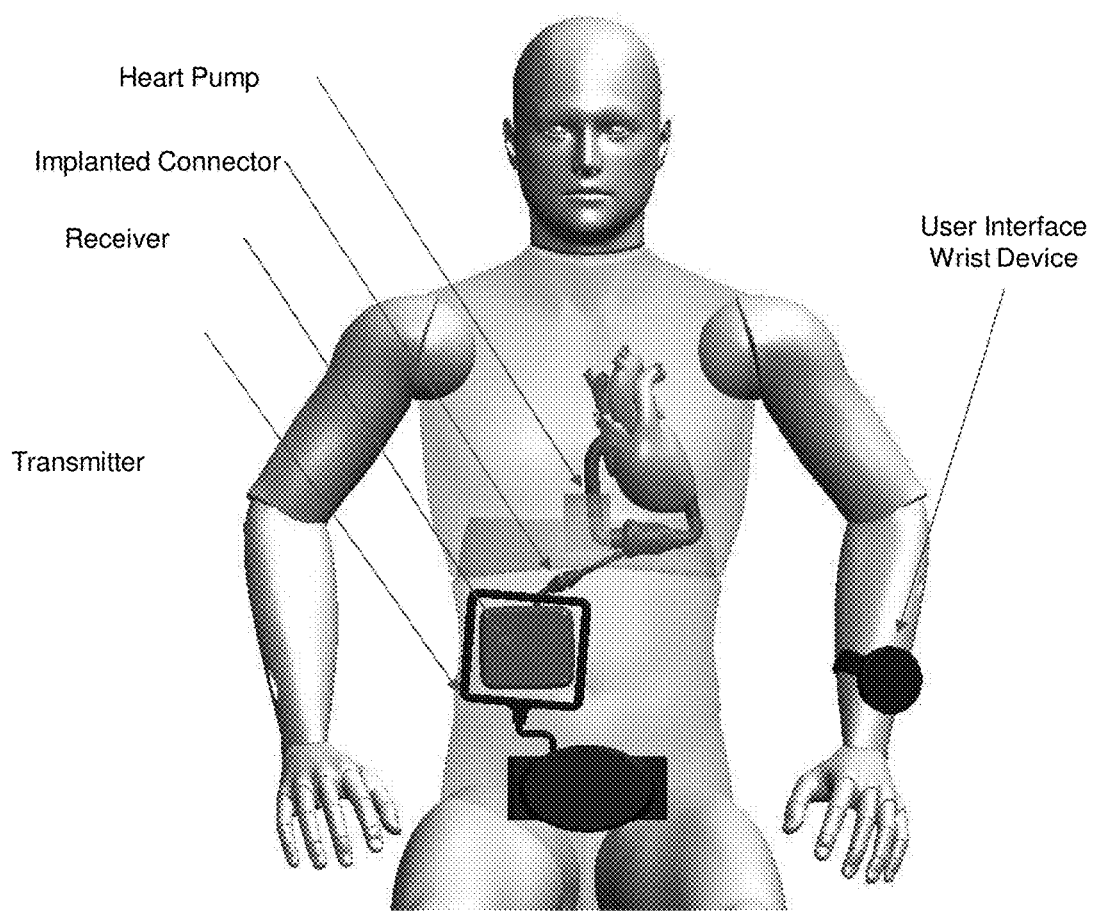

FIGS. 6A and 6B illustrate some of the typical components for a TETS similar to TETS 700 described above. In particular, FIG. 6A shows a few of the external components for power transmission including a transmitter coil 30 powered by batteries 35. The batteries 35 are electrically connected to the coil 30 by user interface (UI) hubs 32 having battery clips 37. The batteries 35 are configured to plug into a corresponding portion of the exemplary battery clips 37 to form the connection to the UI hubs 32. The exemplary system includes two UI hubs 32 for connecting to first and second batteries 35 (e.g., in a "chain" or "daisy-chain" configuration of the batteries 35). One will appreciate, that other configurations may be used to connect the batteries 35 to the coil 30. For example, the '881 publication to Glanzmann et al. incorporated above illustrates embodiments where the external VAD controller includes an integrated battery. The controller can be connected to external batteries, AC mains, or both. Thus, the controller can provide power to the coil using the controller-integrated battery, the external batteries, AC mains, or a combination of the same.

UI hubs 32 include a system computer (not shown) having a screen 33 viewable by patients. The screen 33 is configured to display the system status and other information related to the system and its operation. In an exemplary embodiment, the screen is removable from the UI hub 32.

FIG. 6B illustrates a TET system similar to TETS 700 described above. The system includes external components similar to those shown in FIG. 6A except that it includes a user interface configured as a device to be worn on the wrist. By contrast, the user interface is integrated into the battery hubs in FIG. 6A. The exemplary UI is formed with straps similar to a wrist watch. The UI includes a display (e.g., a screen) and input device. The exemplary UI is configured to monitor the operation of the VAS and/or TET systems. For example, the UI can monitor operation of the internal components—receiver coil, batteries, and/or implantable medical device—and display information to the patient based on the monitored information. The exemplary UI is configured for two-way communication with the internal components. The exemplary UI is configured to program the internal components. For example, the UI may be used to update the firmware or change patient settings. In one embodiment, the internal controller or implantable medical device includes memory and the UI is configured to modify data stored in the memory. In the exemplary case of a VAS, the implantable medical device or controller includes memory for storing patient data and the external UI is used to change the patient settings. Otherwise the patient settings could not be modified without a surgical procedure. The UI can incorporate any of the above-described features in any combination whether the UI is configured as a device to be worn on the wrist (FIG. 6B), as a UI integrated into the battery hubs (i.e., a "UI Hub," shown in FIG. 6A), and/or as any other wearable in any other configuration. In some embodiments, multiple UIs (e.g., one wrist device and one UI hub, two or more UI hubs, etc.) may have distributed control functions. For example, one UI may include an input device (e.g., one or more buttons) and the other may include an output device (e.g., a screen), or one UI may store patient settings and the other may be configured for two-way communication with the implanted components.

Figure 7:
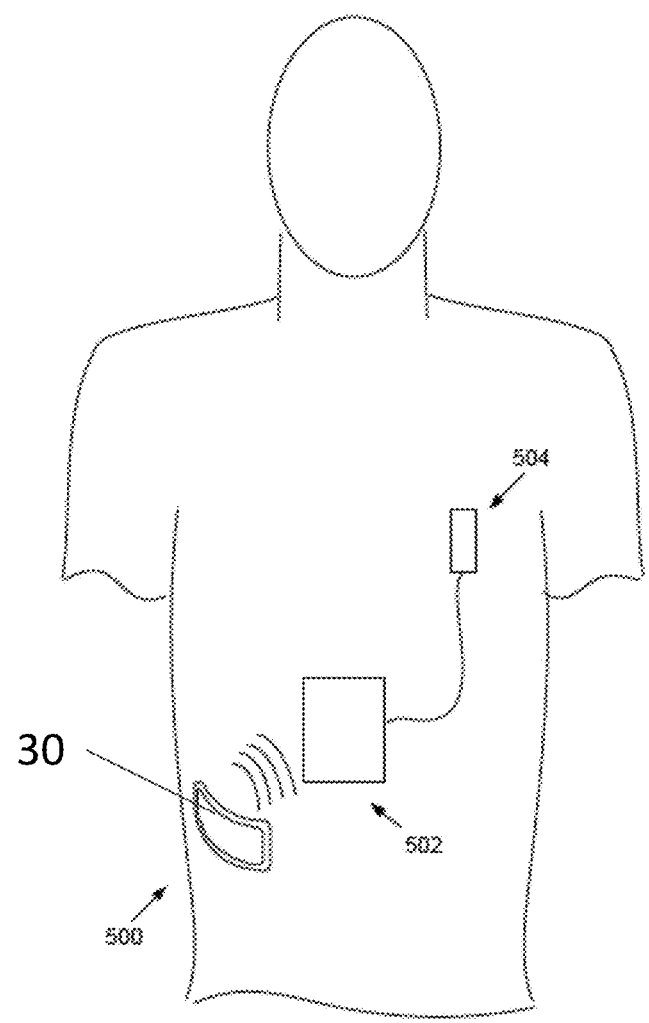
FIG. 7 is a basic configuration of the exemplary TET system, illustrating wireless energy transmission from an external coil to an implanted device.
Figure 8A:
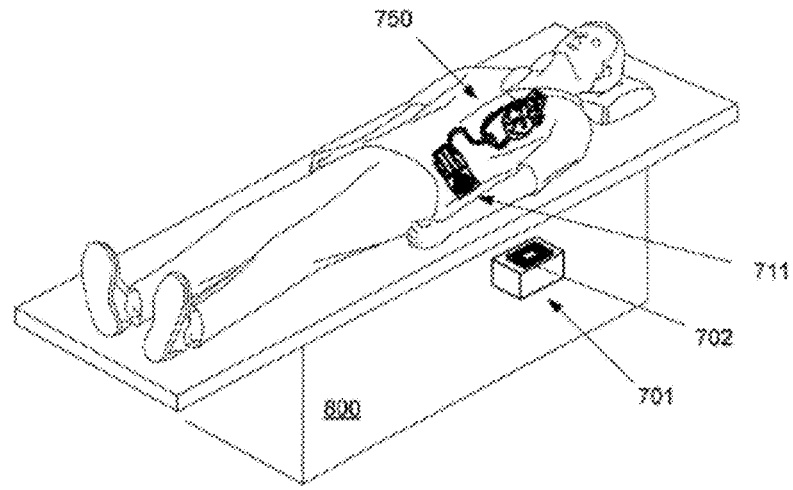
FIGS. 8A and 8B illustrate exemplary uses and orientations with the TET system of FIGS. 5, 6A, and 6B.
Figure 8B:
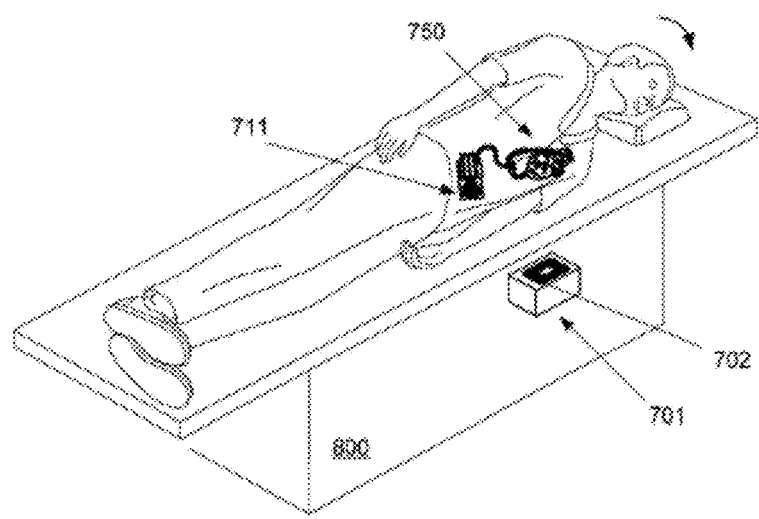

FIGS. 7, 8A, and 8B illustrate the layout and an exemplary use of the TETS components. In FIG. 7, a transmitter coil 30 transmits power to a receiver unit 502 using magnetic resonance, inductance, or other techniques. The receiver unit 502 implanted in the body is connected to a load 504, which may be a VAD or other implantable medical device. The receiver unit may include an internal controller, batteries, electronics, an antenna for data communication, and the like. Alternatively, any of the components may be segregated in different locations within the body.

FIGS. 8A and 8B show an exemplary use of the TETS. In FIGS. 8A and 8B, the transmitter resonator 702 as part of the transmitter unit 701 of the TETS 700 is embedded in a bed 800. Implanted in a patient are a VAD 750 and a receiver unit 711 with a non-planar receiver resonator that is coupled to the rechargeable batteries of the VAD 750. In the exemplary embodiment, the TETS 700 is configured to be "loosely coupled" whereby sufficient power is transmitted between the transmitter and receiver in a variety of orientations and distances. Hence, the TETS 700 is still able to transfer a sufficient amount of energy to recharge the rechargeable batteries of the VAD 750 whether the patient is lying flat on the patient's back on the bed as shown in FIG. 8A or is lying on the patient's side as shown in FIG. 8B.

Figure 9:
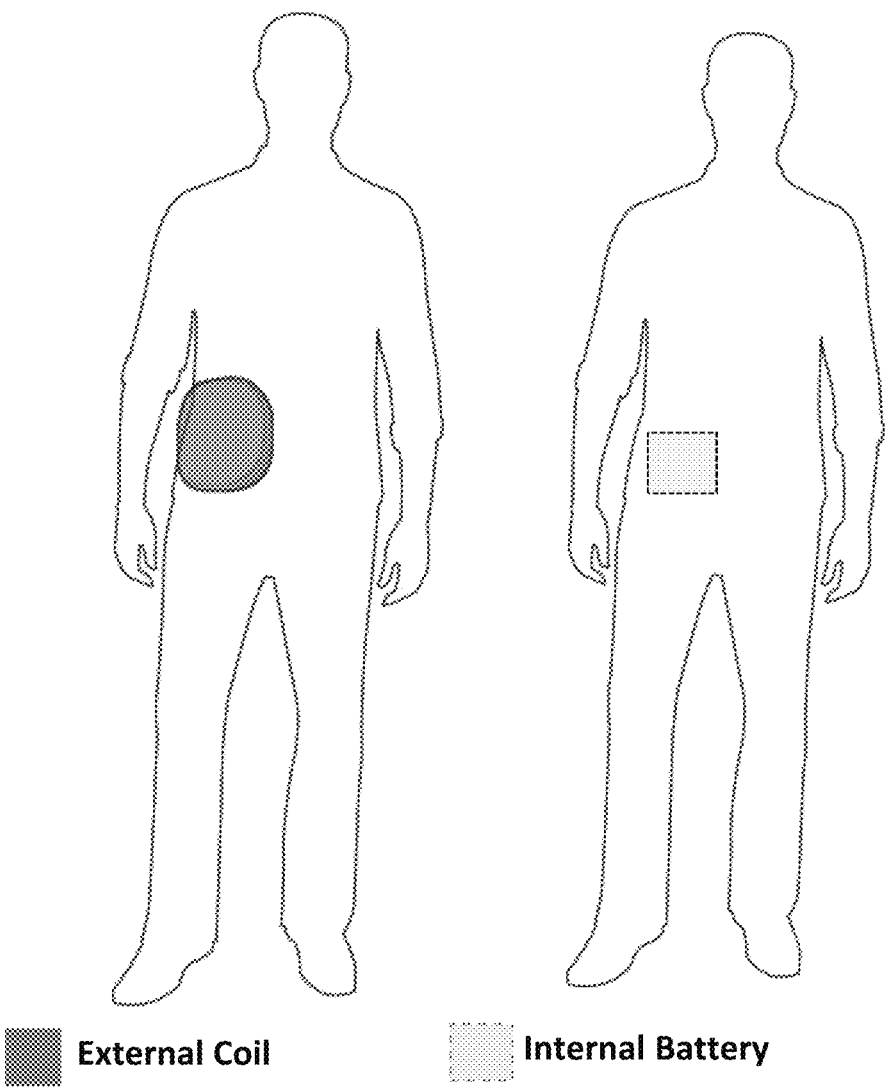
FIG. 9 shows positioning of an external coil and internal battery in accordance with aspects of the invention.
Figures 10A, 10B:
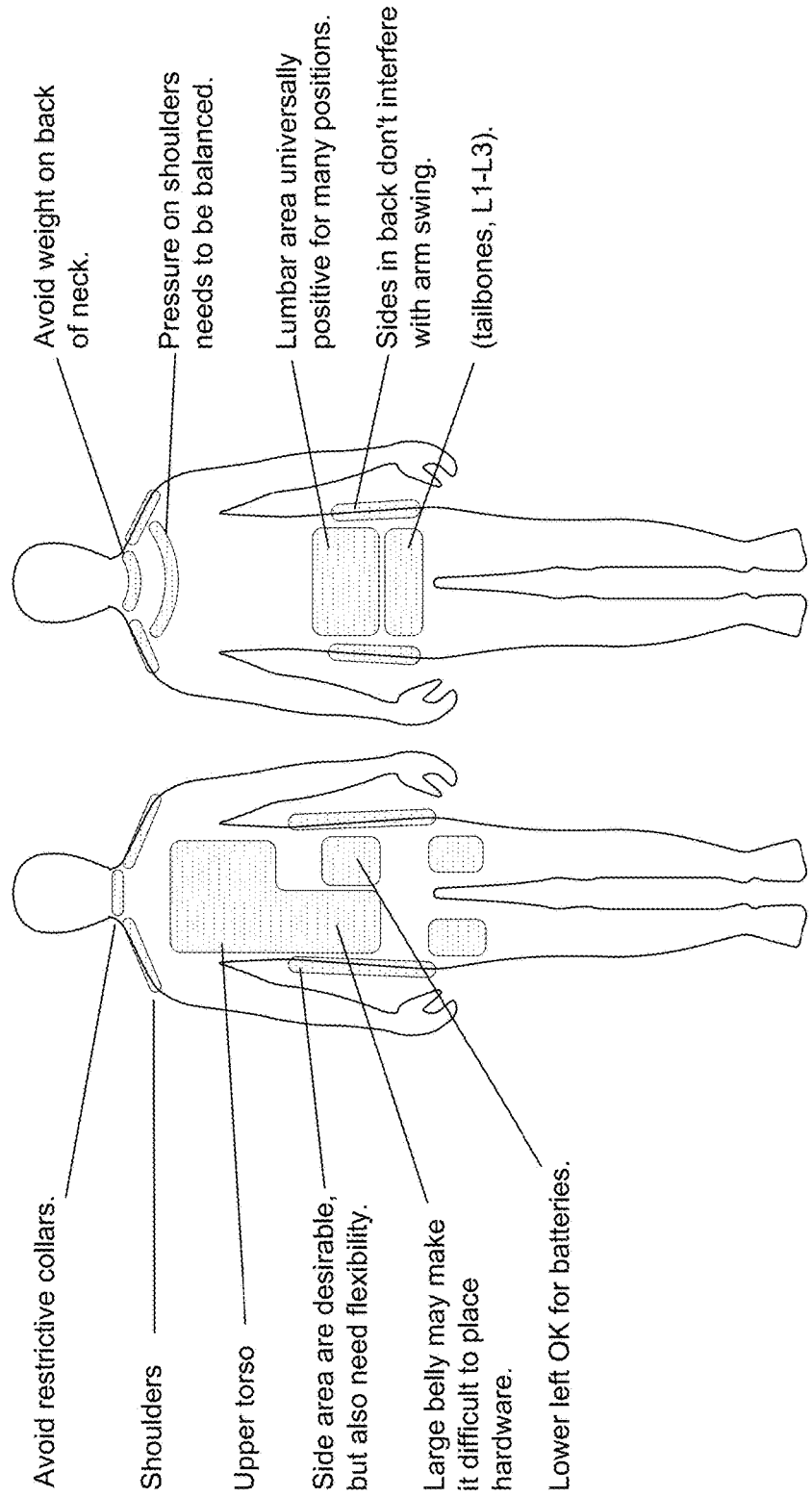
FIGS. 10A and 10B are illustrations of certain potential locations for placement of an external coil, and external peripherals in accordance with aspects of the invention.

Turning to FIGS. 9-10B, the external and internal coils may be positioned in a variety of locations. Generally the closer the external transmitter and internal receiver coils are positioned to each other, the better the coupling and power efficiency. One approach to the design of a TET system is to determine an optimal location for the implanted components including the receiver coil and let the receiver location inform the location of the external transmitter. FIG. 9 illustrates a typical scenario whereby both coils are positioned about the lateral abdominal area. For example, the external coil is placed on the lower abdomen, to the right of midline/belly button. The internal battery is also placed on the lower abdomen, to the right of midline/belly button. The external coil must align with the placement of the internal battery, as described above, although the exact location of the external coil will vary slightly from patient to patient, as the location of the internal battery is determined by the surgeon.

FIGS. 10A and 10B are front and back views, respectively, showing a variety of potential anatomical positions for placement of the various system external components. The components include, but are not limited to, the external transmitter coil and peripherals such as batteries, electronics, a user interface, and a controller. Because the location of some of these external components relate to the position certain internal components, the positions shown in FIGS. 10A and 10B also relate in certain respects to placement of internal components including, but not limited to, the internal receiver coil, battery, TET circuitry, antenna and data communication circuitry, and implantable medical device.

In an exemplary embodiment, the desired position is determined by a wearable device (e.g., jacket, shirt, or straps). The desired position of the coil component depends on the medical device, application, and intended use. For example, some positions are more desirable for holding relatively heavy components. Some positions are sensitive to prolonged pressure. Restrictive collars should be avoided, as should weight on the back of the neck. Any pressure on the shoulders should be balanced. Side areas may be desirable, but also require flexibility of components placed there, and components should not interfere with the swing of the arms. In addition, the lumbar area may be positive for many positions. The strategy for selecting a position of the external coil may also depend on the patient population. One position which works for a patient with a high body mass index (BMI) may be impractical for another patient with a low BMI. Body shape and gender may also be factors. It may be impractical to manufacture individually customized wearable solutions for each patient. Accordingly, one strategy may be to select a position that is desirable for large portion of the patient population and is acceptable for the rest of the population. Another strategy may be to provide a plurality of wearables each with different coil positions for partial customization.

As described above with respect to FIGS. 1 to 4, the position of the coil can be critical to performance, in particular energy transmission, and patient quality of life (QoL). With continued reference to FIGS. 10A and 10B, in one embodiment the system is designed to maintain the coil on the abdomen. With continued reference to FIGS. 10A and 10B, in one embodiment the system is designed to maintain the coil on the abdomen. In one embodiment, the system is designed to maintain the coil laterally on the abdomen. In one embodiment, the system is designed to maintain the coil on the lumbar region of the patient's back.

FIGS. 11A to 28 illustrate a variety of devices for carrying external components of exemplary system mechanical circulatory support (MCS) system, and in particular a ventricular assist system (VAS), making use of wireless energy transfer. Although described in terms of a VAS, one will appreciate that the same principles may be applied equally to other systems using percutaneous wire or wireless energy including, but not limited to, ICDs, neurostimulators, and other medical devices as well as phones, cameras, and other electronics. U.S. Pub. No. 2010/0122995 to Thomas et al., incorporated herein for all purposes by reference, describes wearables and other devices for peripherals with a conventional VAD system configuration. Various aspects of the invention are similar to those described by Thomas et al.

The wearable devices described herein address a number of system and patient needs including, but not limited to, positioning and alignment of the transmitter coil, patient comfort and allowing a wide range of motion, distributing and balancing the weight of the peripherals on the body to reduce strain, stability of components and security, flexibility of configurations, and providing the patient easy access to peripherals during use. For example, as explained above with respect to FIGS. 2, 3A, and 3B, the relative positioning of the transmitter and receiver coils greatly influences the coupling efficiency and plays an important role in the overall effectiveness of the system. The wearable devices may also address other needs such as maintaining a separation distance between the skin and peripheral components which generate heat. For example, in various embodiments the wearable device is designed to separate heat generating components (e.g., the control electronics) from the patient's skin. In various respects, the embodiments described herein seek to optimize patient comfort, QoL, and usability, while also providing good system performance.

Figure 11A:
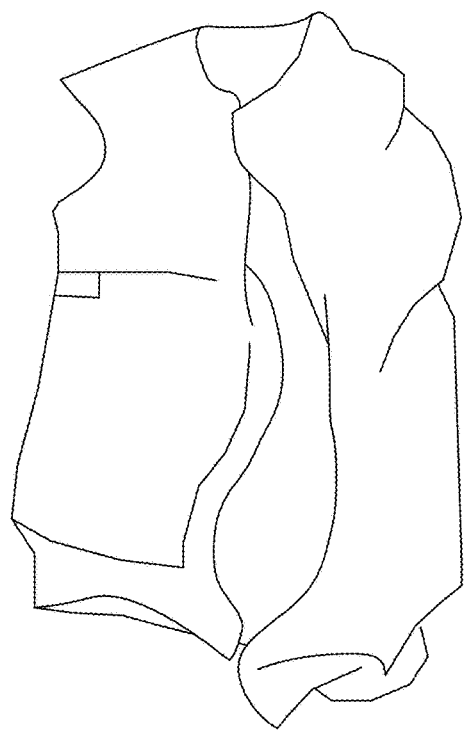
FIG. 11A is a front view of a wearable device for holding the external system components of a VAS and TET system in accordance with the inventions.
Figure 11B:
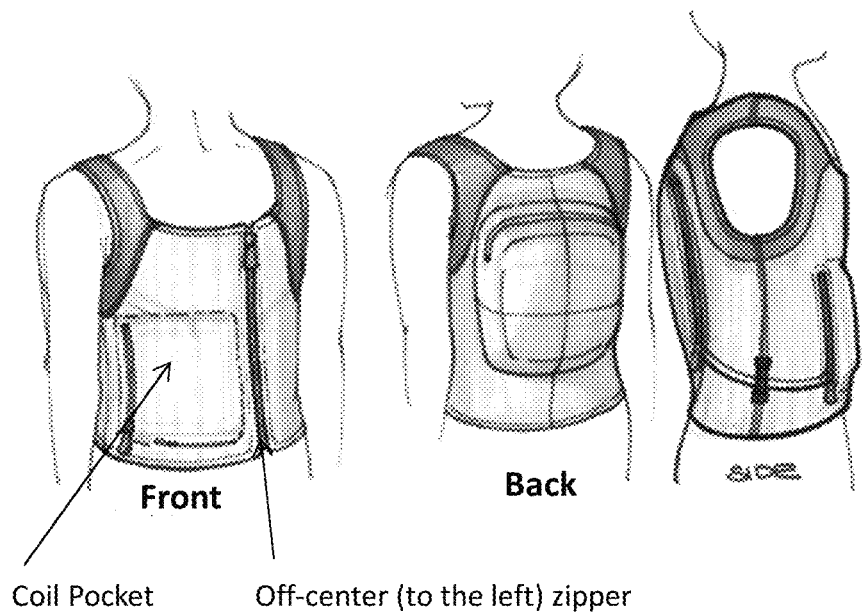
FIG. 11B includes front, back, and side views of the device of FIG. 11A.

FIGS. 11A to 11D illustrate a wearable device for holding the transmitter coil and other peripheral components in accordance with aspects of the invention. The wearable device in FIG. 11A is formed as a vest or shirt. The vest may be provided in different sizes (e.g., small, medium, and large). The exemplary vest is a compression shirt. In one embodiment, a section of the fabric at the breast region is configured to be very stretchy. In one embodiment, a section of the fabric at the breast region is configured to hang relatively loose to provide more comfort around a woman's bra sizes.

Figure 11C:
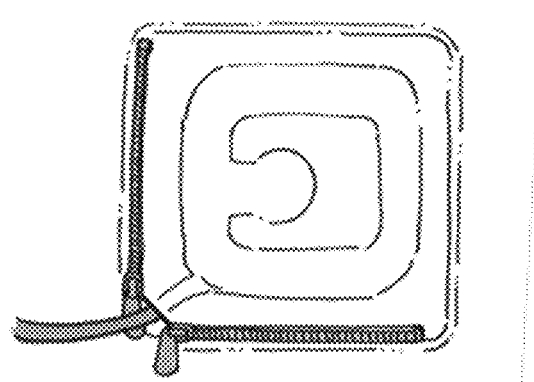
FIG. 11C is an enlarged view of a pocket in the device of FIG. 11A.
Figure 11D:
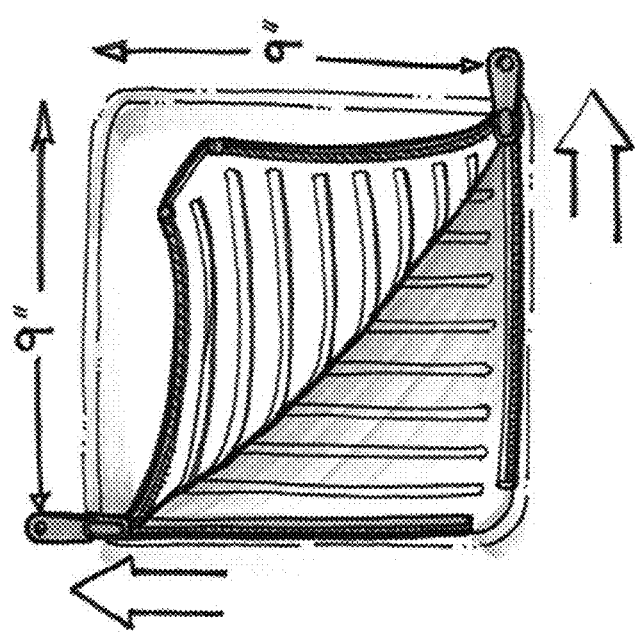
FIG. 11D is an enlarged view of the pocket of FIG. 11C in a partially open position.

As shown in FIGS. 11C and 11D, the exemplary wearable includes a pocket for holding the transmitter coil. The provision of a pocket provides more precision alignment of the coil relative to the patient's body, and in turn the internal components. The pocket includes a zip closure. The closure has two zip closures: one zipper on the side going down and one on the bottom going across. The zip closure allows the patient to easily open a full corner of the pocket and insert the coil. In various embodiments, the closure is a plastic zipper. The plastic zipper may reduce the risk of interference with the coil flux.

In various embodiments, the wearable's pocket is configured so the coil position is adjustable. The sides of the interior can be lined with a "grip" coating or material (e.g., silicone) to hold coil in correct position within the pocket. Padding may be provided for patient comfort. In addition, the pocket may be slightly oversized, so the patient can align it properly and the coil will not shift during wear.

Figure 12A:
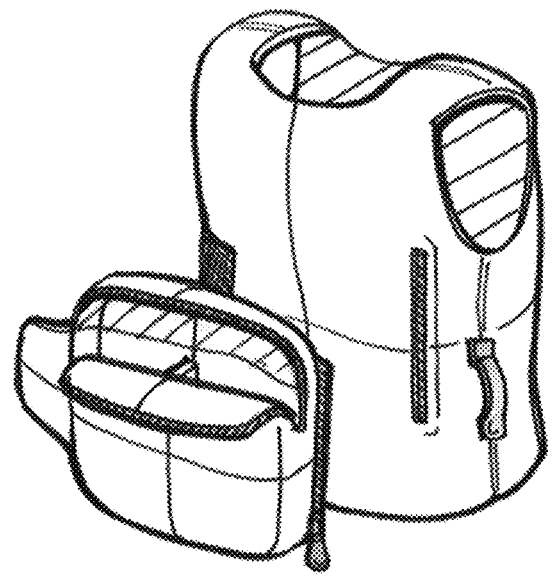
FIGS. 12A and 12B are perspective views of a wearable device similar to the device of FIG. 11A, illustrating a removable battery pocket connected to a body portion by zippers.
Figure 12B:
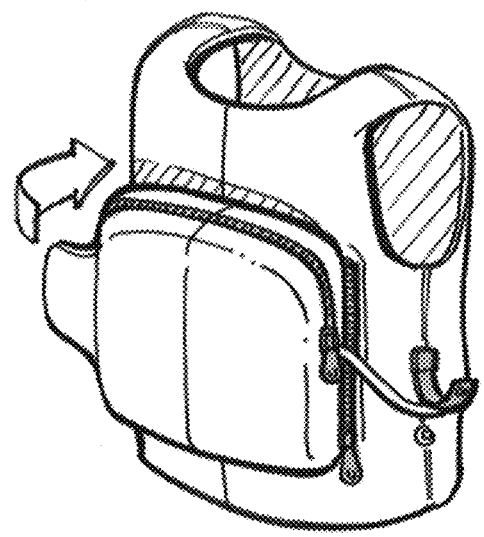
Figure 12C:
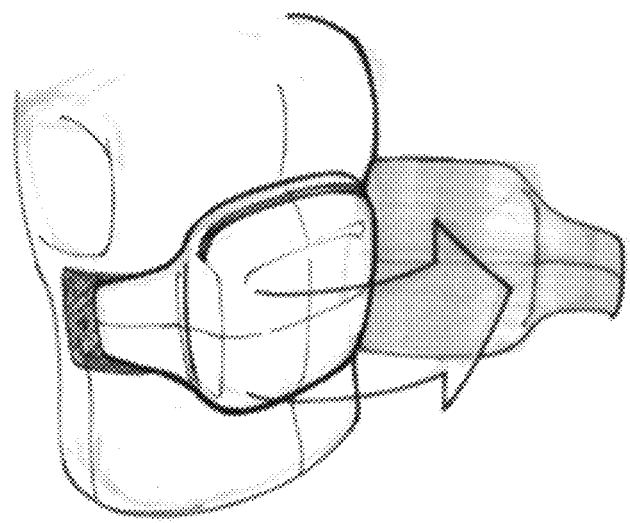
FIG. 12C is a rear view of a wearable device similar to FIG. 12A, illustrating a battery pocket having flaps for attachment.

With reference to FIGS. 12A to 12C, the exemplary wearable may include a battery pocket on the back. The battery pocket is fully removable. The pocket is padded for patient comfort. The pocket is configured so the battery is accessible even while the patient is wearing it.

The exemplary battery pocket design is configured with flaps for attaching the pocket to the patient's body. In order to change the batteries, the patient releases the hook-and-loop fastener on the patient's left side and then swings the battery pocket around to the front thereby enabling the patient to change batteries. In one example, the batteries must be changed periodically so it is advantageous to provide easier battery exchange without requiring removal of the whole wearable. Additionally, a battery pocket zipper attachment allows the patient to remove the battery pocket to wear the shirt for holding the coil during sleep.

Figure 13:
FIG. 13 is a front view of another wearable device similar to the device of FIG. 11A.

FIG. 13 shows another wearable device similar to the one shown in FIG. 11A (e.g., a vest).

Figure 14:
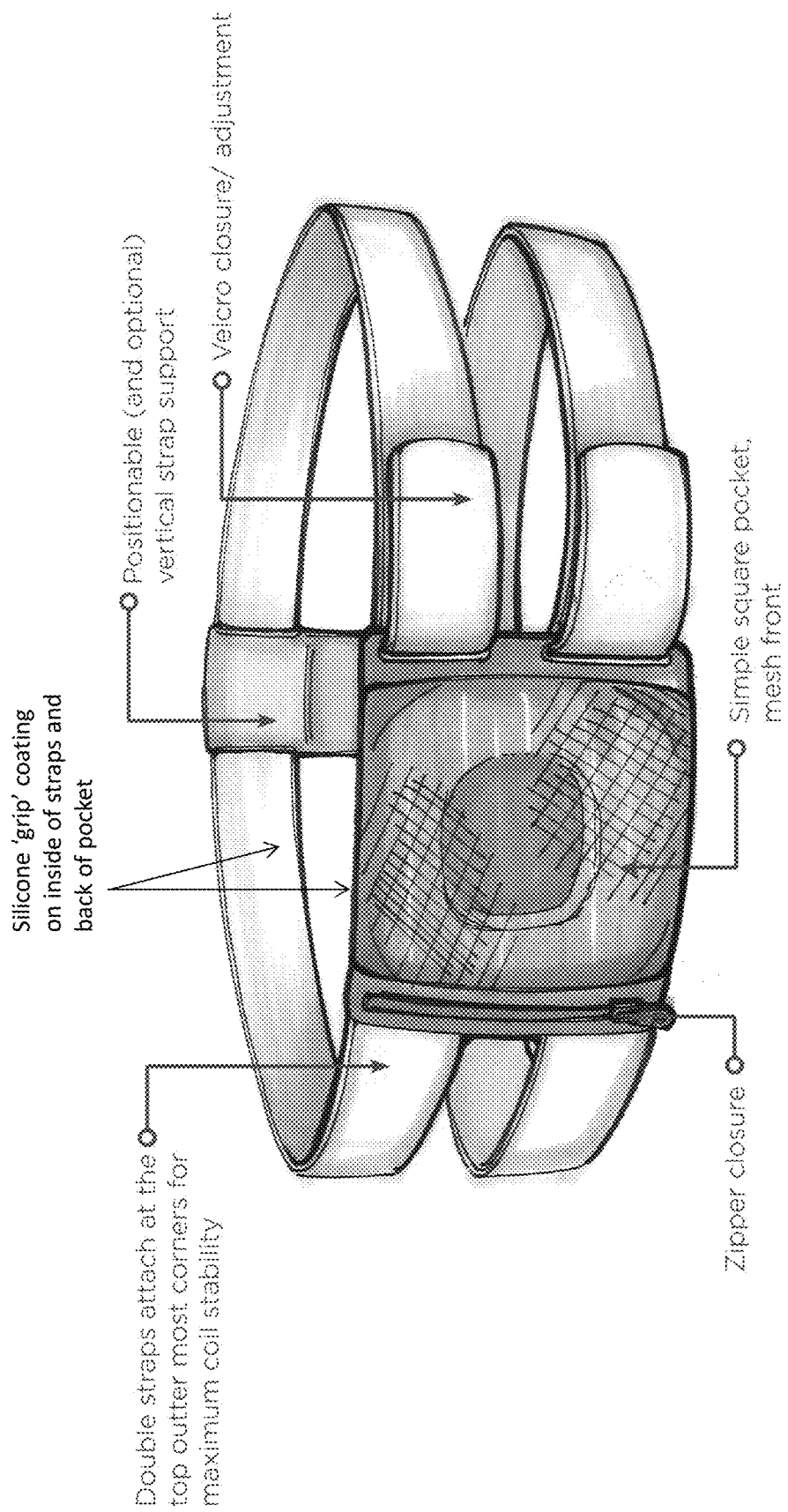
FIG. 14 is a perspective view of a wearable device similar to the device of FIG. 11A, illustrating a pocket and straps for fastening the pocket to a patient's abdominal area or waist.
Figure 15A:
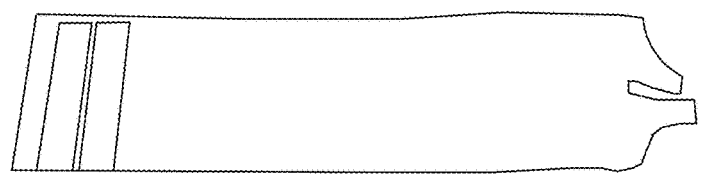
FIGS. 15A to 15E are several views of another wearable device similar to the device of FIGS. 11A and 14, the device formed as an abdominal band.
Figure 15B:
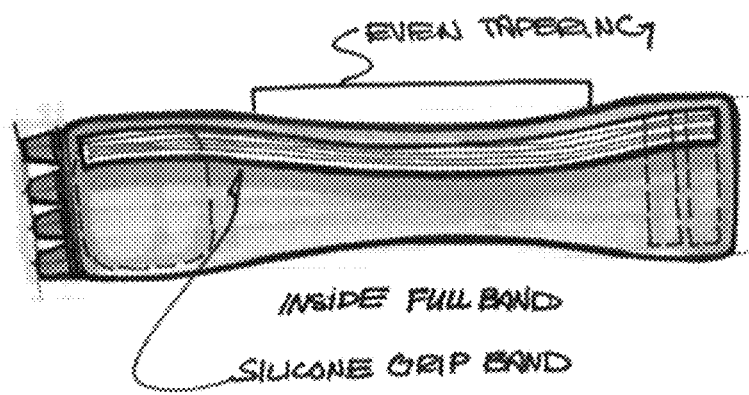
Figures 15C, 15D, 15E:
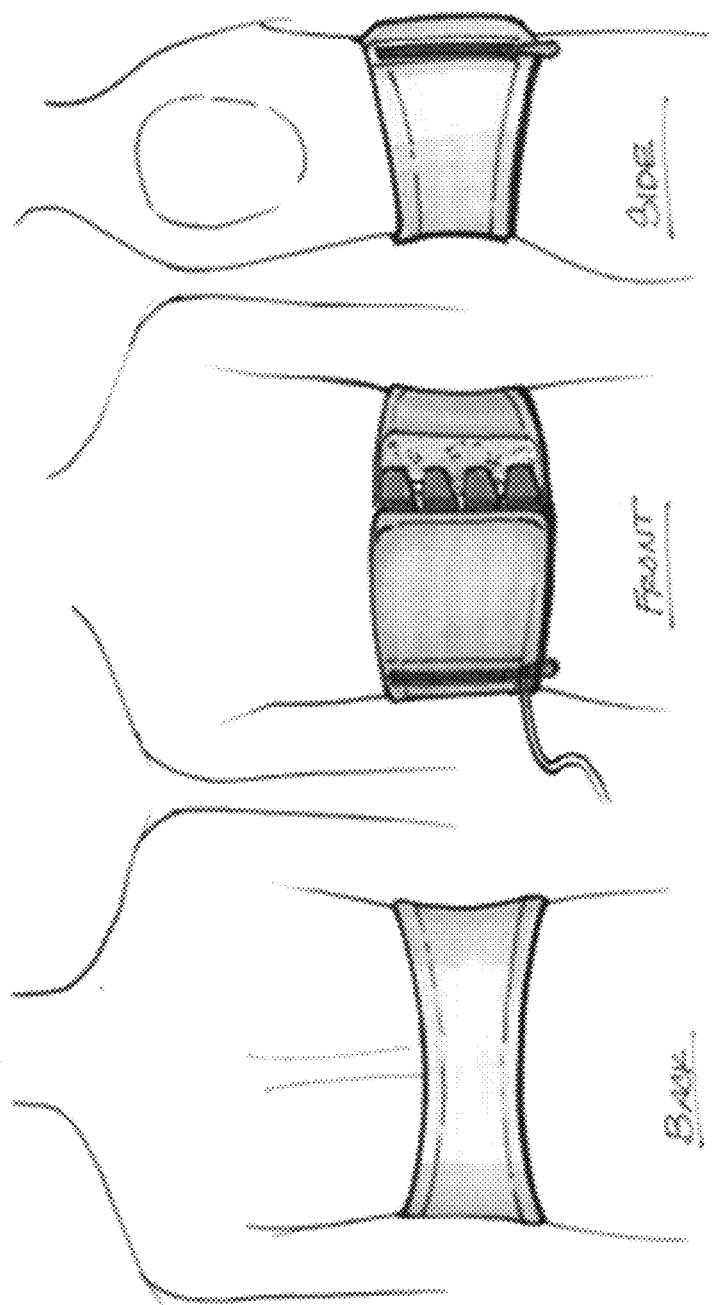
Figure 16:
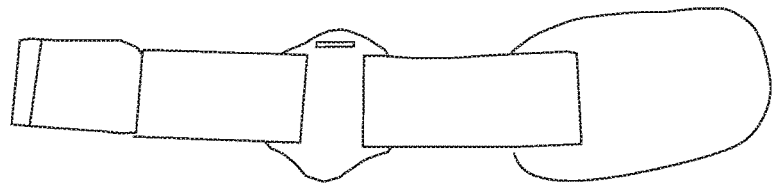
FIG. 16 is a front view of another wearable device similar to the device of FIG. 15A.
Figure 17A:
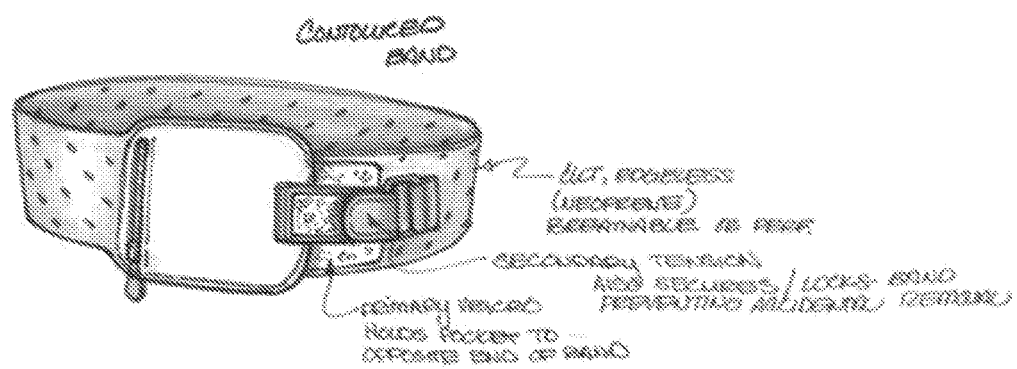

FIG. 14 shows another wearable device formed as a band or belt for wrapping around the patient. The exemplary embodiment is a two-band design. The band is configured to fit a wide range of sizes from a waist size of about 24" to about 40". In various embodiments, the band is configured to fit waist sizes of at least 40". A hook-and-loop fastener on each strap provides size adjustment. The coil is held within a pocket (mesh front) with a zipper closure. Vertical grommets on the pocket to support where the straps loop through the pocket portion. The wearable optionally includes a movable vertical support strap. Horizontal straps may be provided which slide into the vertical support. The wearable is configured with an "edge-less" fabric for patient comfort. For example, standard elastic straps may cause skin irritation in some patients. A set of interior of straps may be included. The straps may have a "non slip" grip coating or material (e.g., silicone) in the inside of the straps (and/or on the back of the pocket).

FIGS. 15A to 15E show another wearable device formed as belt. The belt in FIGS. 15A to 15E is similar in some respects to the band shown in FIG. 14. The belt is configured to allow adjustment of a height of belt and contour of the shape. For example, the belt features even tapering around a middle section thereof. This allows optimization, for example, to eliminate fabric bunching at the back of belt. The coil pocket is provided with a zipper that has been minimized in size. The belt optionally includes a relatively more flexible "loop" section. An interior has a strip of "nonslip" grip coating or material.

Attention is now directed to FIGS. 16 and 17A-17C which show another wearable device. By contrast to the wearables described above, the illustrated embodiment is a wearable for holding the external coil.

The illustrated embodiment is formed as a full coil belt. The belt is formed of a breathable and/or perforated fabric (e.g., neoprene) to reduce heat. In one embodiment, the primary belt fabric has minimal edges (e.g., die cut or welded) to reduce any skin irritation a stitch might create. A secondary tension adjustment is formed in a manner similar to the vest of FIG. 11A.

Figure 18A:
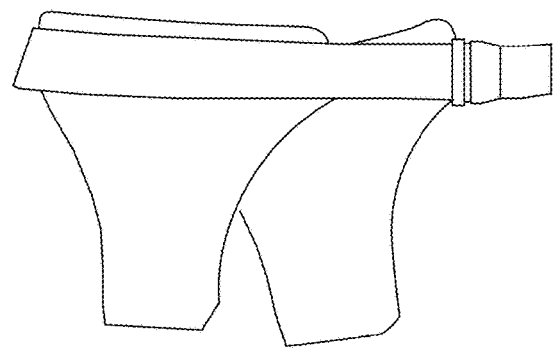
FIGS. 18A and 18B are several views of another wearable device similar to the device of FIG. 11A except the device is configured to hold only the external batteries.
Figure 18B:
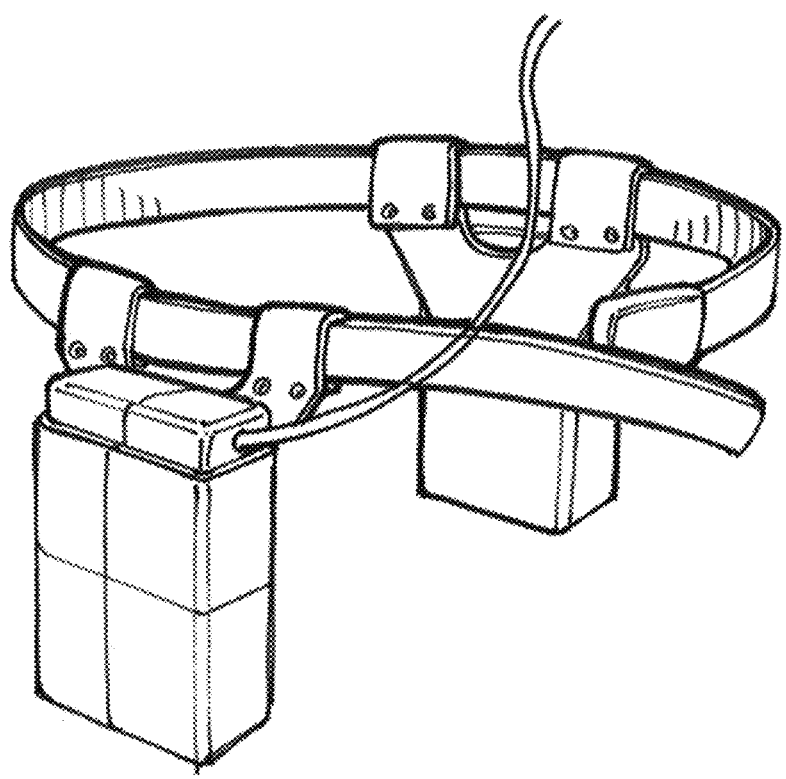

FIGS. 18A and 18B show another wearable device formed as a battery belt. The belt is configured to maintain a large belt attachment point to distribute weight evenly. The belt is split into two or more sections to allow for pant belt loops if patient chooses to use his or her existing pant belt. In one embodiment, the belt is configured so to accommodate an existing pant belt. The exemplary belt is configured to allow adjustment for a waist between about 24" to about 40".

Figure 19A:
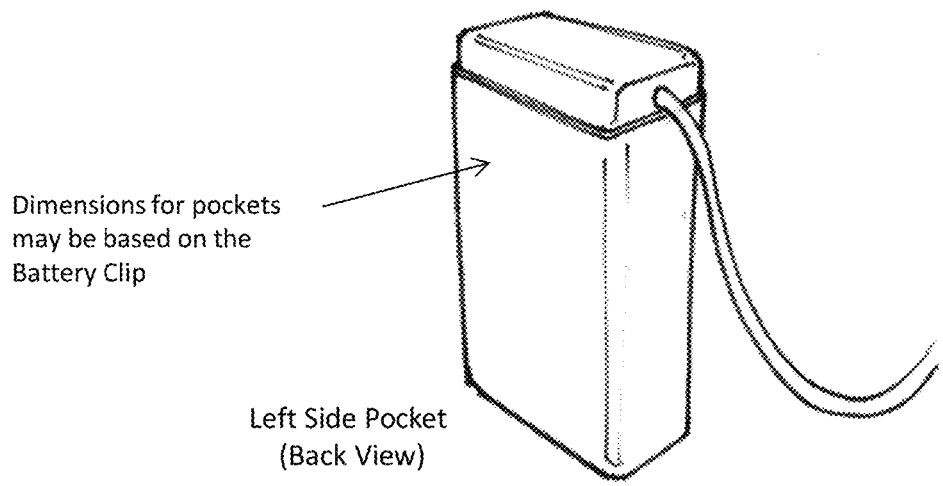
FIGS. 19A and 19B are several views of another wearable device similar to the device of FIGS. 6A, 11A, and 18A.
Figure 19B:
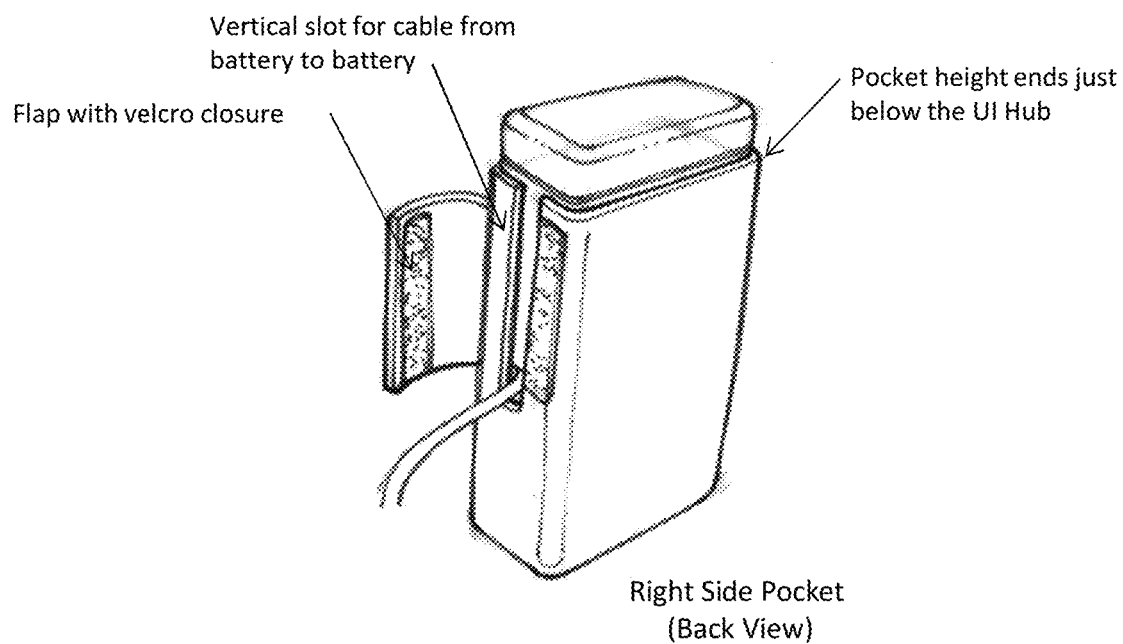

Turning to FIGS. 19A and 19B, the exemplary belt has a battery clip pocket height relatively higher than the pockets described above. For example, the pocket height ends just below the UI hub. The increased height of the battery clip pocket allows for added security so the battery remains stably in the pocket. The battery pocket may also include a vertical slot for connecting a cable between batteries, coverable by a flap (e.g., with a hook-and-loop closure).

Figure 20A:
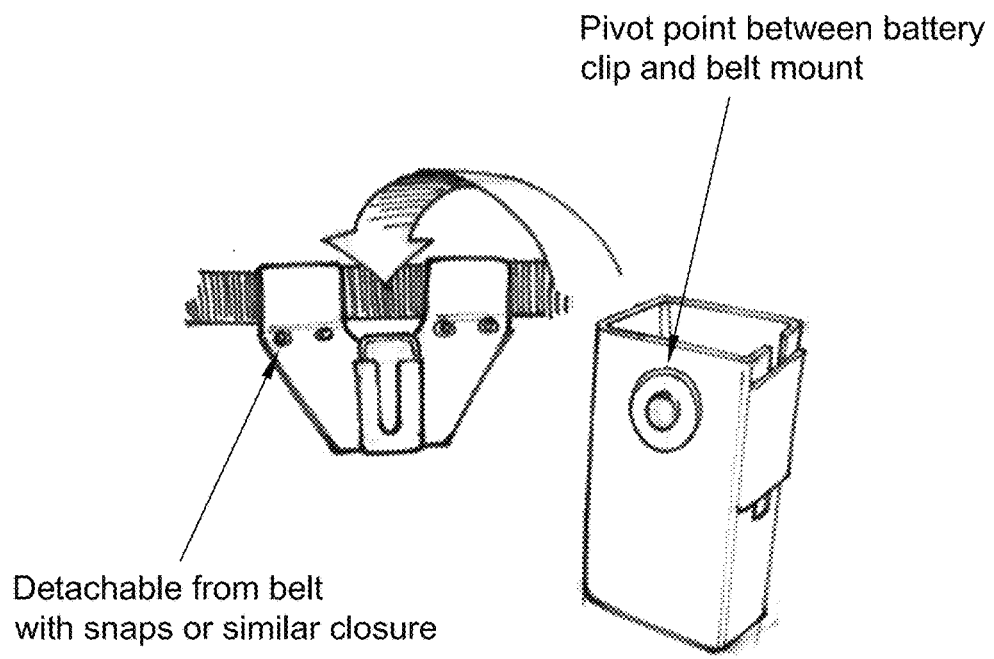
FIGS. 20A and 20B are several views of another wearable device similar to the device of FIG. 19A.
Figure 20B:
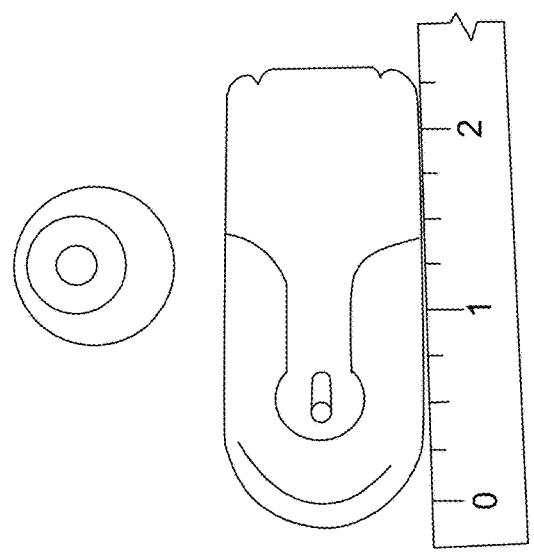

In one embodiment shown in FIGS. 20A and 20B, a pivot or snap is provided between the battery clip pocket and the belt mounting system. The pivot allows the battery clips to rotate for added comfort and move to prevent breakage during use, e.g., when the patient is sitting in a chair.

Figure 21A:
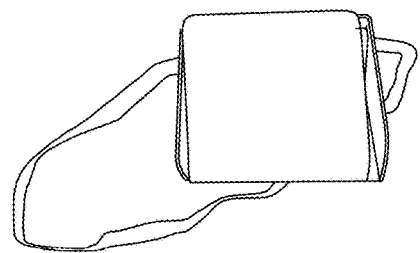
FIGS. 21A and 21B are several views of a shoulder bag for use with a device similar to that of FIG. 11A.
Figure 21B:
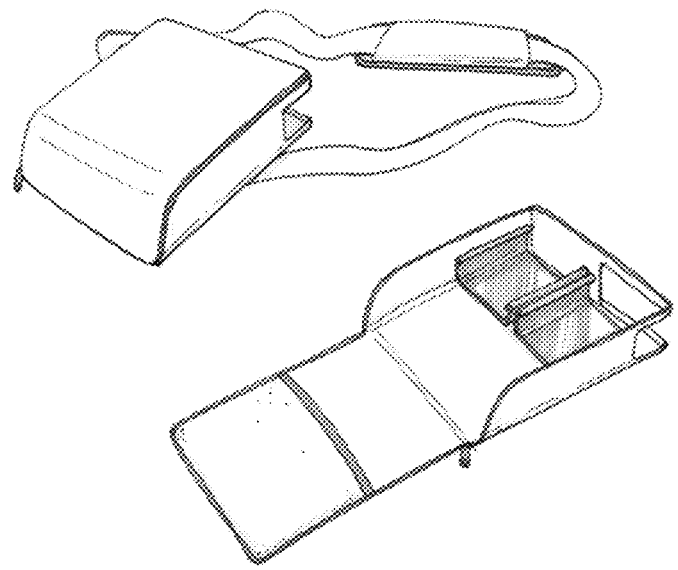
Figure 22:
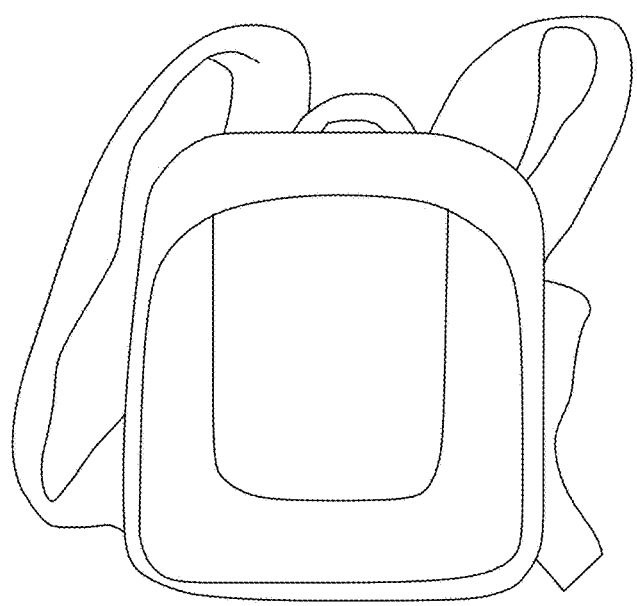
FIG. 22 is a front view of a device similar to that of FIG. 21A, the device formed as a backpack.

FIGS. 21A, 21B, and 22 show another form of a wearable device. The device shown in FIGS. 21A and 22B is a battery bag having a front zipper. The device shown in FIG. 22 is a backpack.

FIGS. 21A and 22B show a battery bag with a front flap that opens to expose an interior. The interior of the bag includes storage compartments and dividers. An internal battery clip mounts so the battery clips are held in place when bag is opened.

The bag includes a padded shoulder strap for carrying. The bag further includes a waist strap stored in a strap storage pocket. The shoulder and waist straps are configured to distribute the weight of the batteries and other items in the bag to reduce strain on the patient.

The illustrated embodiment further includes a UI hub window with additional reinforcement. The exemplary hub window is formed as an opening in the bottom of the bag.

FIG. 22 shows another battery bag. The bag of FIG. 22 is similar to the bag of FIG. 21 except it is formed as a backpack. The bag optionally includes a chest strap to prevent the shoulder straps from slipping off chest. A cut-out window is provided for the UI hub. The bag may include a flap (with clear window) to fold over for security with a hook-and-loop closure. The flap accommodates access to the UI hub and provides visual access to the UI hub for patient during use. An internal divider is provided in the battery compartment.

FIGS. 23A to 28 show additional embodiments of wearable devices in accordance with the invention.

FIGS. 23A-23C show a vest similar in various respects to the wearable device of FIG. 11A. The vest includes a plurality of specific battery pockets to allow the user to choose which ones he or she prefers. The vest may include pocket on the front and/or on the back of the vest. The coil is stored in an internal pouch on the front right panel. A tension belt is hidden between two layers and is used to secure the coil in place. The tension belt may need to be secured (e.g., clipped) before the vest is closed (e.g., zipped). A strap on the user's left side is used to create tension on the coil belt. The wiring between the batteries and coil may be secured on the inside of the vest. The vest may be fabricated from a breathable and/or perforated fabric (e.g., mesh, neoprene) for breathability on skin contact.

FIGS. 24A-24D show a wearable device similar in various respects to the devices of FIG. 11A and the belts described above. The device is formed as a waist belt with the addition of straps. The batteries are clipped to a rigid track which travels around the back and allows the batteries to be positioned where they are most convenient. The belt is adjusted similar to a corset with hooks for the overall sizing, but it can be quickly removed by unzipping the front. The coil sits in a semi rigid cradle and can be pushed up and down for vertical positioning. The cradle moves horizontally for lateral positioning to the left and right. The device is configured so a doctor can aid the user in adjusting the fit of the device on the patient's body, and thereafter the user may make finer, incremental adjustments.

In some embodiments, the garment is configured to provide a mounting track, as shown in FIGS. 24A-24D. The mounting track provides a plurality of mounting points, and is integrally attached to the garment. The mounting track may substantially encompass the thoracic region of the wearer. For example, the mounting track may be positioned on the waist of the wearer. The mounting track is configured to provide at least two mounting positions, and to removably attach to at least one of, a battery, a coil, and/or a pocket (e.g., battery pocket, coil pocket.) The mounting positions may include, but are not limited to, Velcro®, adhesive, magnets, clips, hooks, and the like. In one example embodiment, the mounting positions removably attach to a coil pocket using Velcro®. In another example embodiment, the mounting track is configured to removably couple with a battery by providing a hook and/or a ridge to support the battery. (Velcro is a registered trademark of Velcro Industries BVBA, Deinze, Belgium)

FIGS. 25A-25C show another wearable device similar to the device of FIGS. 23A-24D. The wearable device is embodied as an undershirt, fabricated from a breathable and/or elastic material for comfort of the wearer. The device has a primary portion for wrapping around the waist or chest and a shoulder strap. The shoulder strap maintains the vertical height of the waist band. The shoulder strap also carries some of the weight to alleviate pressure on the waist. The device includes a vertical zipper in for facilitating putting on and taking off the device.

In some embodiments, the garment is configured to provide an adjustable housing, as shown in FIGS. 25A and 25B. The adjustable housing is configured to removably attach at least one of, a battery, an external coil, and a pocket (e.g., coil pocket, battery pocket), to the garment. For example, one or more Velcro® straps may be provided to secure a coil to a garment, by securing the one or more straps after placing the coil under at least one strap. In another example, an elastic strap may be provided to secure a battery, by placing the battery under the midsection of a strap. The adjustable housing is further configured to allow the position of the battery, coil, and/or pocket, to be adjusted by the person wearing the garment. For example, the position may be adjusted with moderate force and may not require additional tools.

In some embodiments, the garment is configured to provide flaps attached at the waist of the garment, and that hang below the waist of the garment wearer, as shown in FIGS. 25A and 25B. The flaps are configured to be removably attached to at least one of, a battery, a coil, and/or a pocket (e.g., battery pocket, coil pocket). In some embodiments, the flaps are configured to pivot at the waist of the garment. For example, the flaps may hang from the garment while the wearer is standing, and pivot to lay in the lap of the garment wearer after sitting. The battery, coil, and/or pocket may be removably attached to the flaps by at least one of, Velcro®, adhesive, magnets, and the like. In some embodiments, the batteries and/or coils may be stored in a fabric case with cable openings.

FIG. 26A and FIG. 26B shows another device similar to the devices of FIGS. 23A-25C except the device is formed as a full vest/undershirt. In some embodiments, the shirt is substantially made of an elastic material, and/or includes tension straps to secure the garment to the wearer. The device is formed to hold snugly against the body so it can be easily fit under normal clothing.

In some embodiments, a dual lock strip is provided, as shown in FIGS. 26A and 26B. The dual lock strip is configured to removably attach to both a pocket containing a coil and/or battery and a garment. The dual lock strip is configured to allow for the placement of the pocket (e.g., external coil pocket, battery pocket) to be adjusted. For example, the pocket may be removed from the dual lock strip and attached to a slightly lower position on the dual lock strip. Additionally or alternatively, the dual lock strip is configured to allow for adjustments to the placement of the dual lock strip on the garment. For example, the dual lock strip, which a pocket may be attached to, may be removed from a garment and attached on a higher portion. In some embodiments, the dual lock strip has a larger attachment surface than the pocket, to allow for the positioning of the pocket to be adjusted. In further embodiments, placement guides are provided on the dual lock strip to indicate proper placement of the dual lock strip on the garment and/or pocket. For example, the dual lock strip may include a visual marker indicating a corresponding location on the garment for proper placement. The dual lock strip may be removably coupled to the garment and/or pocket using one of, Velcro®, adhesive, magnets, and the like.

The exemplary vest does not include pockets for the coil or battery. Instead, illustrated embodiment is intended as a wearable system. A separate carrier is provided for holding the transmitter coil. The carrier is removable from the vest. FIG. 27 shows additional accessories for carrying the batteries. For example, the batteries can be carried in a bag similar to the one shown in FIG. 21B. Battery pockets may also be provided. In the illustrated embodiments, the pockets can be removably attached to the vest. FIG. 28 shows an additional embodiment for holding the batteries. As shown in FIG. 28, the battery pocket and vest can be configured for connection with hook-and-loop fasteners. A portion of the vest includes hook fasteners, and an outer surface of the battery pocket includes loop fasteners or a felt material. Thus, unlike the embodiments above with discrete, predetermined battery locations, the battery pocket can be placed in a variety of customized locations. The exemplary battery pocket is relatively large and can accommodate two or more batteries. One will appreciate from the description herein that other configurations may be used to provide semi-customized configuration of the battery pockets. Additionally, the vest includes a large pocket on the inside of the vest where the external coil may be placed.

While the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

What is claimed is:

1. A system for wireless energy transfer for an implantable medical device, comprising:
    a transmitter coil;
    at least one battery for powering an implantable medical device; and
    a garment to be worn by a patient requiring treatment, the garment comprising:
        a body portion configured for wrapping around at least a thoracic region of a body of the patient; and
        at least one pocket for holding and maintaining the transmitter coil at a desired location relative to the body of the patient.

2. The system of claim 1, further comprising a hub assembly including a hub for attaching to the at least one battery and a wire for connecting the at least one battery to the transmitter coil.

3. The system of claim 2, wherein the hub assembly further includes a user interface.

4. The system of claim 3, wherein the user interface includes a touch screen.

5. The system of claim 3, wherein the user interface is configured to display system information to the patient.

6. The system of claim 1, wherein the garment includes a window corresponding to the hub assembly.

7. The system of claim 6, wherein the window is sized and shaped to allow the patient to access the user interface.

8. The system of claim 1 wherein the at least one pocket for holding and maintaining the transmitter coil is formed of a non-metal material.

9. A garment to be worn by a patient requiring a medical treatment, the garment comprising:
    a transmitter coil in electrical communication with a receiver coil implanted in a patient;
    a body portion configured for wrapping around at least a thoracic region of a body of the patient;
    at least one strap configured to drape over a shoulder of the patient;
    at least one pocket sized and shaped to hold a battery for powering an implantable medical device; and
    at least one pocket for maintaining the transmitter coil at a desired location relative to the body of the patient.

10. The garment of claim 9, wherein the at least one pocket for maintaining the transmitter coil is formed of a non-metal material.

11. The garment of claim 9, wherein the at least one pocket for maintaining the transmitter coil is positionable on a plurality of positions of the body portion.

12. The garment of claim 11, wherein each of the plurality of positions is determined based on an acceptable coupling between the transmitter coil and the receiver coil.

13. The garment of claim 9, wherein the at least one pocket for holding the battery for powering the implantable medical device is positionable on a plurality of positions in a battery attachment region of the body portion.

14. The garment of claim 13, wherein the body portion further includes a coil attachment region, and wherein the at least one pocket for maintaining the transmitter coil is configured to be attached to the body portion with hook and loop fasteners.

15. The garment of claim 14, wherein the coil attachment region and the battery attachment region are at least partially overlapping.

* * * * *